(12) United States Patent
Nguyen et al.

(10) Patent No.: US 8,168,795 B2
(45) Date of Patent: May 1, 2012

(54) SELECTIVE SPHINGOSINE-1-PHOSPHATE RECEPTOR ANTAGONISTS

(75) Inventors: Phong X. Nguyen, Placentia, CA (US); Todd M. Heidelbaugh, Fountain Valley, CA (US); Ken Chow, Newport Coast, CA (US); Michael E. Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 102 days.

(21) Appl. No.: 12/852,768

(22) Filed: Aug. 9, 2010

(65) Prior Publication Data

US 2011/0039866 A1    Feb. 17, 2011

Related U.S. Application Data

(60) Provisional application No. 61/232,997, filed on Aug. 11, 2009.

(51) Int. Cl.
*A61K 31/44* (2006.01)
*C07D 213/46* (2006.01)

(52) U.S. Cl. .......................... 546/314; 514/354

(58) Field of Classification Search .................. None
See application file for complete search history.

(56) References Cited

U.S. PATENT DOCUMENTS

| 4,952,683 A | 8/1990 | Tschannen |
| 5,102,901 A | 4/1992 | Wijngaarden |
| 5,110,987 A | 5/1992 | Liotta |
| 5,294,722 A | 3/1994 | Kim |
| 5,403,851 A | 4/1995 | D'Orlando |
| 5,580,878 A | 12/1996 | D'Orlando |
| 6,235,912 B1 | 5/2001 | Takesako |
| 6,239,297 B1 | 5/2001 | Takesako |
| 2007/0191313 A1 | 8/2007 | Beard |
| 2009/0088420 A1 | 4/2009 | Neamati |
| 2009/0163545 A1 | 6/2009 | Goldfarb |

FOREIGN PATENT DOCUMENTS

| WO | WO 02/062761 A1 | 8/2002 |
| WO | WO 2004/110352 A2 | 12/2004 |
| WO | WO 2009/026407 A1 | 2/2009 |
| WO | WO 2010/019646 A1 | 2/2010 |

OTHER PUBLICATIONS

Dayam, Raveendra, et al.; "Diketo Acid Pharmacophore 2. Discovery of Structurally Diverse Inhibitors of HIV-1 Integrase"; Journal of Medicinal Chemistry; vol. 48, pp. 8009-8015; 2005.
Riordan; Stammer et al, "o-Chloranil Oxidation of Azlactones"; Tetrahedron Letters, vol. 16, pp. 1247-1250; 1976.
J. M. Riordan, "o-Chloranil-azlactone adducts and their conversions to unsaturated amino acid derivatives"; Journal of Organic Chemistry; vol. 42, pp. 236-240; 1977.

*Primary Examiner* — Janet Andres
*Assistant Examiner* — Heidi Reese
(74) *Attorney, Agent, or Firm* — Doina G. Ene; John E. Wurst; Kevin J. Forrestal

(57) ABSTRACT

Described herein are compounds useful as antagonists of sphingosine-1-phosphate receptors. Further described herein is the use of these compounds and related pharmaceutical compositions to treat disorders associated with sphingosine-1-phosphate-3 (S1P3) receptor modulation.

19 Claims, No Drawings

SELECTIVE SPHINGOSINE-1-PHOSPHATE RECEPTOR ANTAGONISTS

CROSS-REFERENCE

This application claims the benefit of U.S. Provisional Patent Application Ser. No. 61/232,997, filed on Aug. 11, 2009, the entire disclosure of which is incorporated herein by this specific reference.

FIELD OF THE INVENTION

Described herein are compounds useful as antagonists of sphingosine-1-phosphate receptors. Use of these compounds and pharmaceutical compositions including these compounds in treating disorders associated with sphingosine-1-phosphate 3 (S1P3) receptor modulations are described.

BACKGROUND

A sphingolipid is a lipid having important roles within a living body. Various sphingolipids, having sphingosine as a constituent, are widely distributed within a living body, including within the nervous system on the surface cell membranes. Sphingosine is a compound having the chemical structure

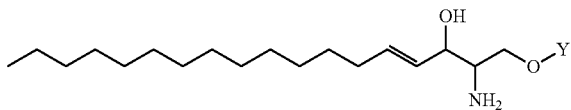

wherein Y is hydrogen. Sphingolipids present on cell membranes function to regulate cell growth; participate in the development and differentiation of cells; function in nerves; are involved in the infection and malignancy of cells; and the like.

Many of the physiological roles of sphingolipids remain to be solved. However, it is known that lipidosis, for example, is caused by accumulation of a particular sphingolipid in the body. Further, it has recently been discovered that ceramide, a derivative of sphingosine, potentially has an important role in the mechanism of cell signal transduction, and studies about its effect on apoptosis and cell cycle have been reported.

Sphingosine-1-phosphate, for example, is an important cellular metabolite, derived from ceramide that is synthesized de novo or as part of the sphingomyeline cycle (in animal cells). Sphingosine-1-phosphate has also been found in insects, yeasts and plants.

The enzyme, ceramidase, acts upon ceramides to release sphingosine, which is phosphorylated by sphingosine kinase, a ubiquitous enzyme in the cytosol and endoplasmic reticulum, to form sphingosine-1-phosphate. The reverse reaction can also occur by the action of sphingosine phosphatases, and the enzymes act in concert to control the cellular concentrations of sphingosine-1-phosphate. In plasma, sphingosine-1-phosphate concentrations can reach 0.2 to 0.9 µM, and is found in association with the lipoproteins, especially high density lipoproteins (HDL). It should also be noted that sphingosine-1-phosphate formation is an essential step in the catabolism of sphingoid bases.

Like its precursors, sphingosine-1-phosphate is a potent messenger molecule that perhaps uniquely operates both intra- and inter-cellularly, but with very different functions from ceramides and sphingosine. The balance between these various sphingolipid metabolites may be important for health. For example, within the cell, sphingosine-1-phosphate promotes cellular division (mitosis) as opposed to cell death (apoptosis), which it inhibits. Intracellularly, sphingosine-1-phosphate also functions to regulate calcium mobilization and cell growth in response to a variety of extracellular stimuli. It is suggested that the balance between sphingosine-1-phosphate and ceramide and/or sphingosine levels in cells is critical for their viability. In common with the lysophospholipids, especially lysophosphatidic acid, with which it has some structural similarities, sphingosine-1-phosphate exerts many of its extra-cellular effects through interaction with five specific G protein-coupled receptors on cell surfaces. These are important for the growth of new blood vessels, vascular maturation, cardiac development, cardiac immunity, and for directed cell movement.

Sphingosine-1 phosphate is stored in relatively high concentrations in human platelets, which lack the enzymes responsible for its catabolism. Sphingosine-1 phosphate is released into the blood stream upon activation of physiological stimuli, such as growth factors, cytokines, and receptor agonists and antigens. It might also play a critical role in platelet aggregation and thrombosis, and could aggravate cardiovascular disease. Alternatively, the relatively high concentration of the sphingosine-1 phosphate in HDL may have beneficial implications for atherogenesis. For example, there are recent suggestions that sphingosine-1-phosphate, together with other lysolipids such as sphingosylphosphorylcholine and lysosulfatide, are responsible for beneficial clinical effects of HDL by stimulating the production of the potent antiatherogenic signaling molecule nitric oxide by the vascular endothelium. In addition, similar to lysophosphatidic acid, sphingosine-1 phosphate is a marker for certain types of cancer, and there is evidence that sphingosine-1 phosphate's role in cell division and proliferation may have an influence on the development of cancers. These are currently topics that are attracting great interest amongst medical researchers, and the potential for therapeutic intervention in sphingosine-1-phosphate metabolism is under active investigation.

Further, fungi and plants have sphingolipids and the major sphingosine contained in these organisms has the formula

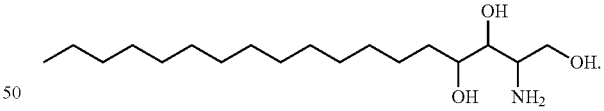

These lipids have important roles in the cell growth of fungi and plants, but details of the roles remain to be solved.

Derivatives of sphingolipids and their related compounds exhibit a variety of biological activities through inhibition or stimulation of metabolic pathways. These compounds include inhibitors of protein kinase C, inducers of apoptosis, immuno-suppressive compounds, antifungal compounds, and the like. Substances having these biological activities can be useful compounds for treating various diseases.

Derivatives of sphingosine have been prepared in various patents. For example, see U.S. Pat. Nos. 4,952,683; 5,110,987; 6,235,912 and 6,239,297. Also, compounds which are similar to some sphingosine derivatives, but which are not reported as being ligands for the sphingosine receptors, are reported in various patents and published patent applications.

See for example, U.S. Pat. Nos. 5,294,722; 5,102,901; 5,403,851 and 5,580,878, and U.S. Patent Application Publication No. U.S. 2003/0125371.

SUMMARY

Described herein are compounds that are useful as sphingosine-1-phosphate (S1P) antagonists. These compounds are useful in treating a wide variety of disorders associated with modulation of S1P receptors. These compounds are useful for the treatment of humans with diseases and conditions that are alleviated by S1P modulation, such as S1P2 and S1P3 receptor modulations, and in particular, use as S1P3 antagonists. The compounds described herein can be, in one example embodiment, substituted picolinamines and substituted benzamides. Further, pharmaceutically acceptable salts, hydrates, solvates, crystal forms and individual isomers, enantiomers, and diastereomers thereof of the compounds described herein can be utilized.

In one embodiment described herein, compounds are described having the structure

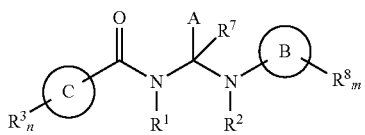

wherein $R^1$ and $R^2$ are each independently selected from H and $C_1$-$C_4$ alkyl;
C is a phenyl, aryl or heteroaryl having the structure

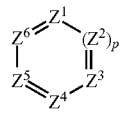

wherein the dashed line represents the presence or absence of a bond, and wherein p is 0-1, and $Z^1$-$Z^6$ are each independently selected from C, N, O or S;

$R^3$ and $R^8$ are each independently selected from H, $C_1$-$C_6$ straight or branched chain alkyl, alkenyl, or alkynl, alkoxy (such as $O(C_1$-$C_6$)), —OH, halogen, —$NR^4_2$, —CN, —$CO_2R^4$, —$C(O)NR^4R^5$, —$CH_2OH$, —$CF_3$, —$OCHF_2$, —$OCF_3$, —$NO_2$, alkylamino, or alkylcarboxyl;

m is 0-5;
n is 0-5;

$R^4$ and $R^5$ are each independently selected from H, $C_1$-$C_6$, branched or unbranched alkyl, alkenyl, or alkynl, $C_3$-$C_6$ saturated or unsaturated cyclic hydrocarbon, aryl, heteroaryl, haloalkyl, hydroxyl, alkoxyl, hydroxyalkyl, alkylcarbonyl, formyl, oxycarbonyl, carboxyl, alkyl carboxylate, alkylamide, alkylamino aminocarbonyl, or amino;

A is $CR^6_3$, $CXR^6_2$, $CX_2R^6$, $CX_3$, $COQ^1$, $SOQ^1$, $SO_2Q^1$, $CSQ^1$, phenyl, substituted phenyl, heterocylic, heteroaromatic, cycloalkyl, cycloalkenyl sulfonyl, sulfone, sulfonamide, sulfoxide, ester, or thiocarbonyl;

X is a halogen;

$R^6$ is H, $C_1$-$C_6$ straight or branched chain alkyl, alkenyl, or alkynyl, haloalkyl, perfluorinated alkyl, partially fluorinated alkyl, perhalogenated alkyl, partially halogenated alkyl, phenyl, substituted phenyl, heteroaryl, cyano, ketyl, and the like;

$Q^1$ is an aryl or heteroaryl variably substituted with $(R^3)_n$, a phenyl, heteroaromatic or cycloalkyl, cycloalkenyl, or partially saturated or saturated heterocyclic ring a bicyclic compound, $NR^4R^5$;

$R^7$ is H, $C_1$-$C_6$ branched or unbranched alkyl, alkenyl, or alkynl, haloalkyl, aryl, heteroaryl, perfluorinated alkyl and partially fluorinated alkyl, phenyl, cyano, ketyl, $CF_3$, substituted aryl or heteroaryl or spirocyclic compounds; and B is phenyl, aryl, heteroaromatic or cycloalkyl, cycloalkenyl, or partially saturated or saturated heterocyclic ring, or a bicyclic compound, with the proviso that when A is $CX_3$, B is not phenyl.

In one example embodiment, $R^1$ and $R^2$ are H; C is aryl or heteroaryl having the structure

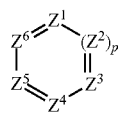

wherein p is 0 or 1, and $Z^1$-$Z^6$ are each independently selected from C, N, O and S; $R^3$ and $R^8$ are halogen; m is 0-2; n is 0-2; A is $COQ^1$, $SOQ^1$, $SO_2Q^1$, $CSQ^1$, amide, sulfonyl, sulfone, sulfonamide, sulfoxide, ester, or thiocarbonyl; $Q^1$ is an aryl or heteroaryl variably substituted with $(R^3)_n$, a phenyl, heteroaromatic or cycloalkyl, cycloalkenyl, or partially saturated or saturated heterocyclic ring a bicyclic compound, $NR^4R^5$; $R^7$ is H; and B is phenyl, heteroaromatic or cycloalkyl, cycloalkenyl, or partially saturated or saturated heterocyclic ring, or a bicyclic compound.

In another example embodiment, C is pyridyl; A is $COQ^1$; $Q^1$ is an aryl or heteroaryl variably substituted with $(R^3)_n$; and B is phenyl.

In yet another example embodiment, the compound has a structure selected from:

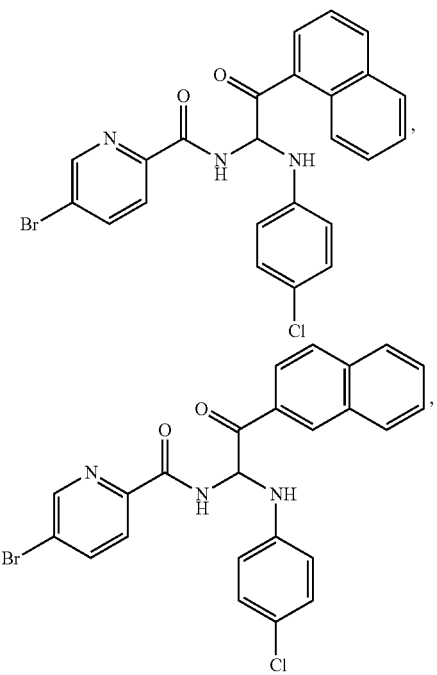

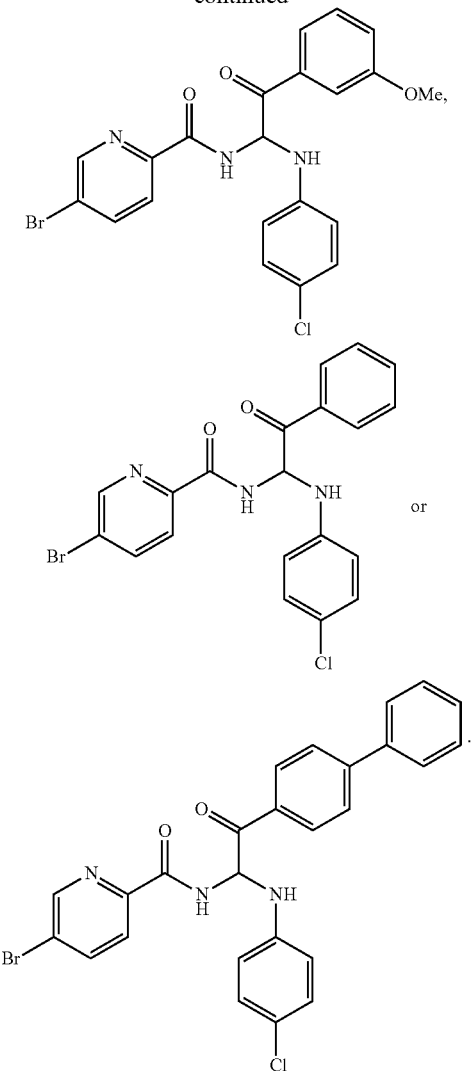

In one example embodiment described herein, a compound is described wherein $R^1$ and $R^2$ are H; C is aryl or heteroaryl having the structure

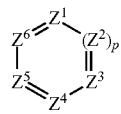

wherein p is 0 or 1, and $Z^1$-$Z^6$ are each independently selected from C, N, O and S; $R^3$ and $R^8$ are halogen; m is 0-2; n is 0-2; A is $CR^6_3$, $CXR^6_2$, $CX_2R^6$, $CX_3$; X is a halogen; $R^6$ is H, $C_1$-$C_6$ straight or branched chain alkyl, alkenyl, or alkynl, haloalkyl, perfluorinated alkyl, partially fluorinated alkyl, phenyl, substituted phenyl, heteroaryl, cyano, ketyl, and the like; $R^7$ is H; and B is phenyl, aryl, heteroaromatic or cycloalkyl, cycloalkenyl, or partially saturated or saturated heterocyclic ring, or a bicyclic compound, with the proviso that when A is $CX_3$, B is not phenyl.

In another example embodiment, m is 0-2; n is 0-2; A is $CR^6_3$, $CXR^6_2$, $CX_2R^6$; X is a halogen; $R^6$ is perfluorinated alkyl or partially fluorinated alkyl, perhalogenated alky or partially halogenated alkyl; and B is phenyl, aryl, or heteroaromatic.

In yet another example embodiment, $R^3$ is bromine and $R^8$ is halogen or methyl.

In yet another example embodiment, the compound has a structure selected from:

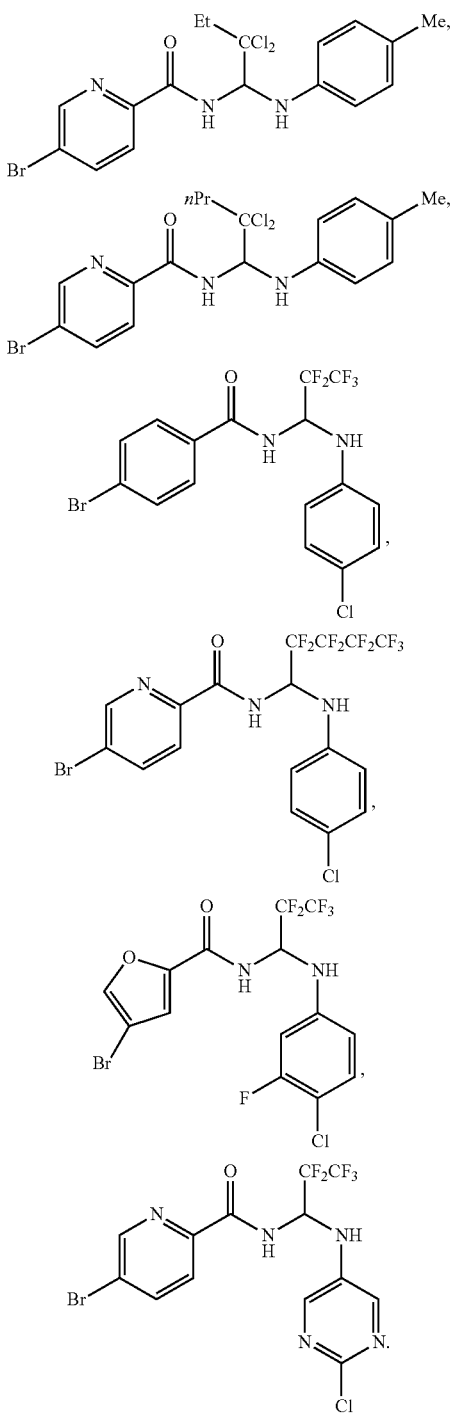

In one example embodiment, wherein $R^1$ and $R^2$ are each independently selected from H and $C_1$-$C_4$ alkyl;

C is a phenyl, aryl or heteroaryl having the structure

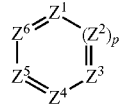

p is 0-1, and $Z^1$-$Z^6$ are each independently selected from C, N, O or S;

$R^3$ and $R^8$ are each independently selected from H, $C_1$-$C_6$ straight or branched chain alkyl, alkenyl, or alkynl, alkoxy (such as $O(C_1$-$C_6))$, —OH, halogen, —$NR^4_2$, —CN, —$CO_2R^4$, —$C(O)NR^4R^5$, —$CH_2OH$, —$CF_3$, —$OCHF_2$, —$OCF_3$, —$NO_2$, alkylamino, or alkylcarboxyl;

m is 0-2;

n is 0-2;

$R^4$ and $R^5$ are each independently selected from H, $C_1$-$C_6$, branched or unbranched alkyl, alkenyl, or alkynl, $C_3$-$C_6$ saturated or unsaturated cyclic hydrocarbon, aryl, heteroaryl, haloalkyl, hydroxyl, alkoxyl, hydroxyalkyl, alkylcarbonyl, formyl, oxycarbonyl, carboxyl, alkyl carboxylate, alkylamide, alkylamino aminocarbonyl, or amino;

A is phenyl, substituted phenyl, heterocylic, heteroaromatic, cycloalkyl, or cycloalkenyl;

$R^7$ is H, $C_1$-$C_6$ branched or unbranched alkyl, alkenyl, or alkynl, haloalkyl, aryl, heteroaryl, perfluorinated alkyl and partially fluorinated alkyl, phenyl, cyano, ketyl, $CF_3$, substituted aryl or heteroaryl; and B is phenyl, aryl, heteroaromatic or cycloalkyl, cycloalkenyl, or partially saturated or saturated heterocyclic ring, or a bicyclic compound.

In another example embodiment, the compound has a structure selected from

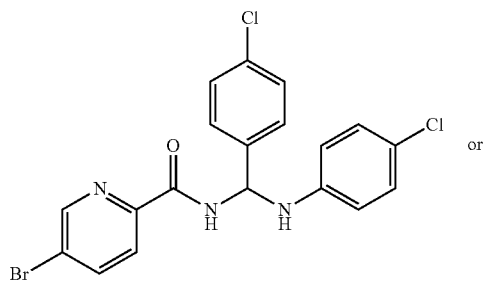

or

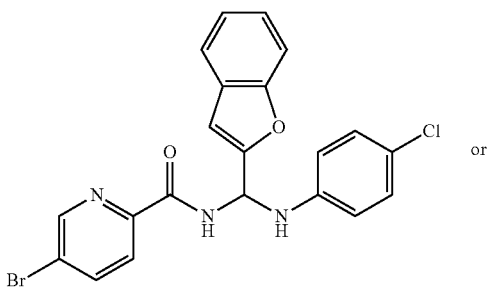

or

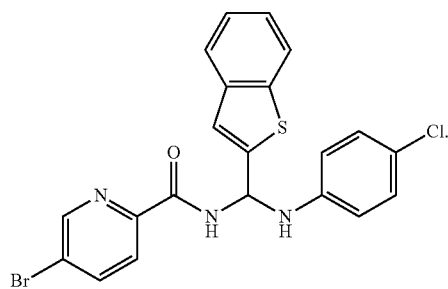

Further described herein in one embodiment is a compound having a structure selected from

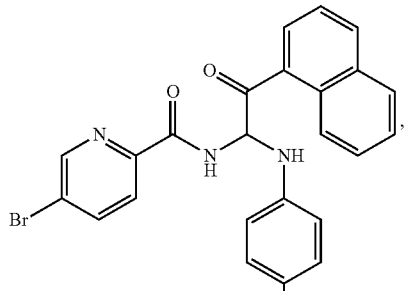

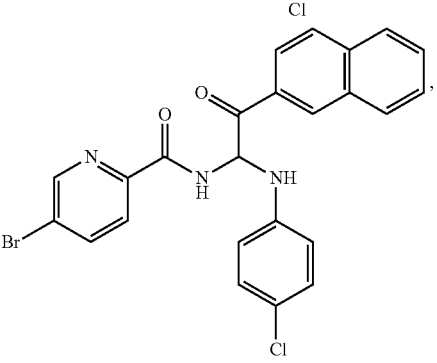

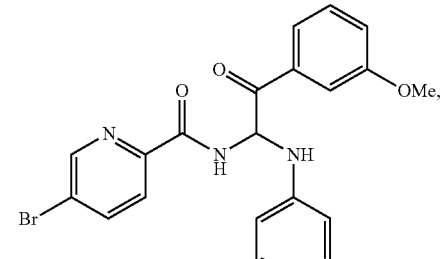

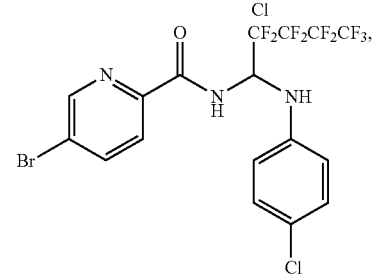

-continued

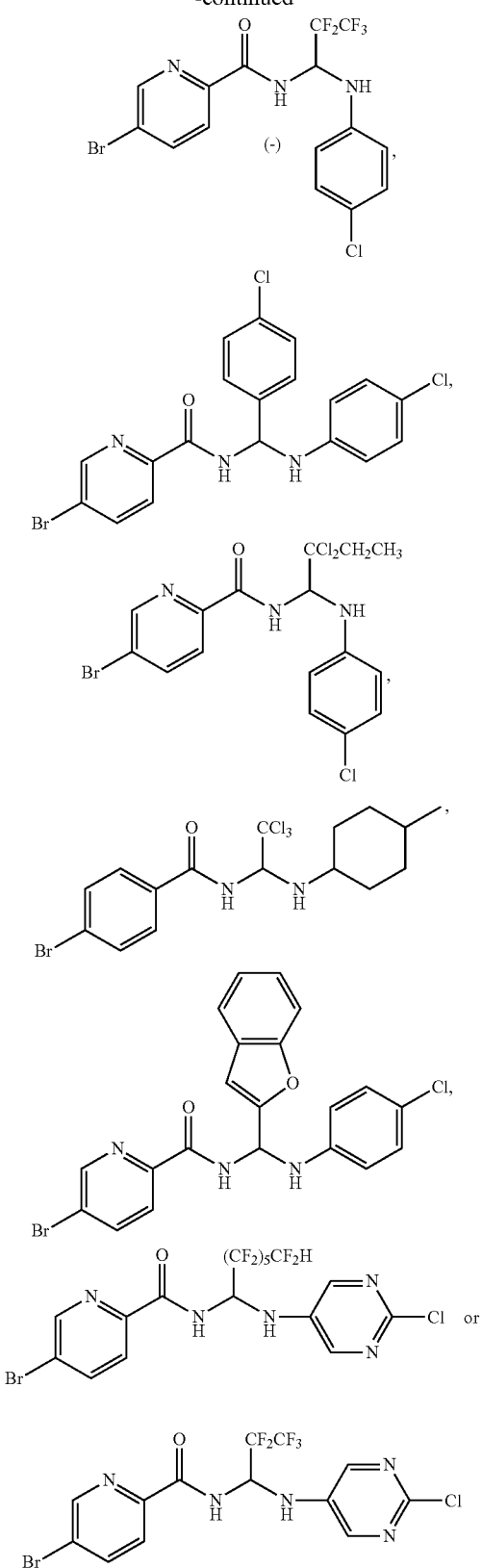

Also described herein are compositions comprising a pharmaceutically acceptable amount of a compound as described herein.

DEFINITION OF TERMS

Certain terms as used in the specification are intended to refer to the following definitions, as detailed below. Where the definition of terms departs from the commonly used meaning of the term, applicant intends to utilize the definitions provided below, unless specifically indicated.

As used herein, "alkyl" refers to straight, branched chain or cyclic hydrocarbyl groups having from 1 to about 100 carbon atoms. Whenever it appears herein, a numerical range, such as "1 to 100" or "$C_1$-$C_{100}$", refers to each integer in the given range; e.g., "$C_1$-$C_{100}$ alkyl" means that an alkyl group may comprise only 1 carbon atom, 2 carbon atoms, 3 carbon atoms, etc., up to and including 100 carbon atoms, although the term "alkyl" also includes instances where no numerical range of carbon atoms is designated. As used herein, "substituted alkyl" refers to alkyl moieties bearing substituents typically selected from alkyl, alkenyl, alkynyl, hydroxy, alkoxy, heterocyclic, aryl, heteroaryl, aryloxy, halogen, haloalkyl, cyano, nitro, amino, lower alkylamino, lower dialkylamino, amido, azido, acyl (—C(O)R$^9$), alkoxymethyl, mercapto (—S—R$^9$), sulfoxy (—S(O)—R$^9$), sulfonyl (—S(O)$_2$—R$^9$), sulfonamide (—S(O)$_2$N(R$^9$)$_2$), carbonate (—OC(O)—O—R$^9$), oxyacyl (—OC(O)—R$^9$), carboxyl (—C(O)ON), ester (—C(O)OR$^9$), carbamate (—OC(O)—N(R$^9$)$_2$), wherein R$^9$ is H or lower alkyl, lower alkenyl, lower alkynyl, aryl, heteroaryl, heterocycle, and the like. As used herein, "lower alkyl" refers to alkyl moieties having from 1 to about 6 carbon atoms.

As used herein, "alkenyl" refers to straight, branched chain or cyclic hydrocarbyl groups having at least one carbon-carbon double bond, and having in the range of about 2 up to about 100 carbon atoms, and "substituted alkenyl" refers to alkenyl groups further bearing one or more substituents as set forth above. As used herein, "lower alkenyl" refers to alkenyl moieties having from 1 to about 6 carbon atoms.

As used herein, "alkylacyl" refers to an alkyl ketone such as ethanone, propanone, and the like.

As used herein, "alkynyl" refers to straight or branched chain hydrocarbyl groups having at least one carbon-carbon triple bond, and having in the range of about 2 up to about 100 carbon atoms, and "substituted alkynyl" refers to alkynyl groups further bearing one or more substituents as set forth above. As used herein, "lower alkynyl" refers to alkynyl moieties having from 2 to about 6 carbon atoms.

As used herein, "aryl" refers to aromatic groups having in the range of 6 up to 14 carbon atoms and "substituted aryl" refers to aryl groups further bearing one or more substituents as set forth above.

As used herein, "cycloalkyl" refers to cyclic (i.e., ring-containing) alkyl moieties typically containing in the range of about 3 up to about 8 carbon atoms, and "substituted cycloalkyl" refers to cycloalkyl groups further bearing one or more substituents as set forth above.

As used herein, "halogen" or "halide" refers to fluoride, chloride, bromide or iodide. The terms "fluoro", "chloro", "bromo", and "iodo" may also be used when referring to halogenated substituents, for example, "trifluoromethyl."

As used herein, "heteroaryl" refers to aromatic moieties containing one or more heteroatoms (e.g., N, O, S, or the like) as part of the ring structure and having in the range of 5 up to 14 total atoms in the ring structure (i.e., carbon atoms and heteroatoms). "Substituted heteroaryl" refers to heteroaryl groups further bearing one or more substituents as set forth above.

As used herein, "heterocyclic" or "heterocycle" refers to non-aromatic cyclic (i.e., ring-containing) groups containing one or more heteroatoms (e.g., N, O, S, or the like) as part of the ring structure, and having in the range of 3 up to 14 carbon atoms and "substituted heterocyclic" or "substituted heterocycle" refers to heterocyclic groups or heterocycles further bearing one or more substituents as set forth above.

As used herein, "hydroxyalkyl" refers to alkyl-OH, such as hydroxymethyl, hydroxyethyl, and the like.

As used herein, "pharmaceutically acceptable salt" refers to any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt. Further, pharmaceutically acceptable salt refers to those salts which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

As used herein "prodrug" refers to a compound which is converted to a therapeutically active compound after administration, and the term should be interpreted as broadly herein as is generally understood in the art. While not intending to limit the scope of the present description, conversion may occur by hydrolysis of an ester group or some other biologically labile group. Generally, but not necessarily, a prodrug is inactive or less active than the therapeutically active compound to which it is converted. Ester prodrugs of the compounds disclosed herein are contemplated. An ester may be derived from a carboxylic acid of $C_1$ (i.e. the terminal carboxylic acid of a natural prostaglandin), or an ester may be derived from a carboxylic acid functional group on another part of the molecule, such as on a phenyl ring. While not intending to be limiting, an ester may be an alkyl ester, an aryl ester, or a heteroaryl ester.

As used herein, "tautomer" refers to the migration of protons between adjacent single and double bonds. The tautomerization process is reversible. Compounds described herein can undergo any possible tautomerization that is within the physical characteristics of the compound. The following is an example tautomerization that can occur in compounds described herein:

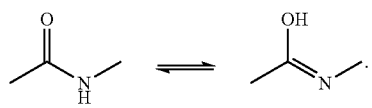

As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

DETAILED DESCRIPTION OF THE INVENTION

Described herein are compounds that are useful as sphingosine-1-phosphate (S1P) antagonists, and therefore, are useful in treating a wide variety of disorders associated with modulation of S1P receptors or are useful for the treatment of humans with diseases and conditions that are alleviated by S1P modulation, and in particular use as S1P3 antagonists. The compounds described herein can be, in one example embodiment, substituted picolinamines and substituted benzamides.

In one example embodiment described herein, compounds are described having the structure

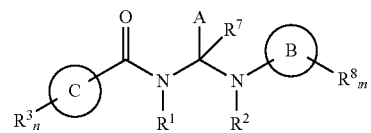

wherein $R^1$ and $R^2$ are each independently selected from H, $C_1$-$C_4$ alkyl;

C is a phenyl, aryl or heteroaryl having the structure

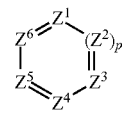

wherein a dashed line represents the presence or absence of a bond and wherein p is 0-1, and $Z^1$-$Z^6$ are each independently selected from C, N, O or S;

$R^3$ and $R^8$ are each independently selected from H, $C_1$-$C_6$ straight or branched chain alkyl, alkenyl, or alkynl, alkoxy (such as $O(C_1$-$C_6$)), —OH, halogen, —$NR^4_2$, —CN, —$CO_2R^4$, —$C(O)NR^4R^5$, —$CH_2OH$, —$CF_3$, —$OCHF_2$, —$OCF_3$, —$NO_2$, alkylamino, or alkylcarboxyl;

m is 0-5;

n is 0-5;

$R^4$ and $R^5$ are each independently selected from H, $C_1$-$C_6$, branched or unbranched alkyl, alkenyl, or alkynl, $C_3$-$C_6$ saturated or unsaturated cyclic hydrocarbon, aryl, heteroaryl, haloalkyl, hydroxyl, alkoxyl, hydroxyalkyl, alkylcarbonyl, formyl, oxycarbonyl, carboxyl, alkyl carboxylate, alkylamide, alkylamino aminocarbonyl, or amino;

A is $CR^6_3$, $CXR^6_2$, $CX_2R^6$, $CX_3$, $COQ^1$, $SOQ^1$, $SO_2Q^1$, $CSQ^1$, amide, sulfonyl, sulfone, sulfonamide, sulfoxide, ester, thiocarbonyl, phenyl, substituted phenyl, heterocylic, heteroaromatic, cycloalkyl, or cycloalkenyl;

X is a halogen;

$R^6$ is H, $C_1$-$C_6$ straight or branched chain alkyl, alkenyl, or alkynl, haloalkyl, perfluorinated alkyl, partially fluorinated alkyl, perhalogenated alkyl, phenyl, substituted phenyl, heteroaryl, cyano, ketyl, or the like;

$Q^1$ is an aryl or heteroaryl variably substituted with $(R^3)_n$, a phenyl, heteroaromatic or cycloalkyl, cycloalkenyl, or partially saturated or saturated heterocyclic ring a bicyclic compound, $NR^4R^5$;

R[7] is H, $C_1$-$C_6$ branched or unbranched alkyl, alkenyl, or alkynl, haloalkyl, aryl, heretoaryl, perfluorinated alkyl and partially fluorinated alkyl, phenyl, cyano, ketyl, $CF_3$, substituted aryl or heteroaryl or spirocyclic compounds; and B is a variably substituted phenyl, heteroaromatic or cycloalkyl, cycloalkenyl, or partially saturated or saturated heterocyclic ring, or a bicyclic compound.

Further, pharmaceutically acceptable salts, hydrates, solvates, crystal forms and individual isomers, enantiomers, or diastereomers thereof of the above compounds are contemplated.

In one example embodiment, when A is $CX_3$, for example in the structure

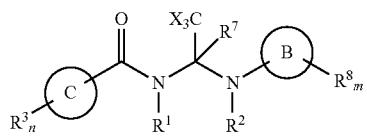

then B is not phenyl.

Another example embodiment includes the following structure

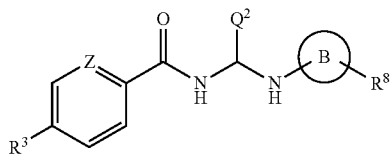

wherein $Q^2=C(O)Q^1$ where $Q^1$ is primarily the carbon ring.

Some example compounds include:

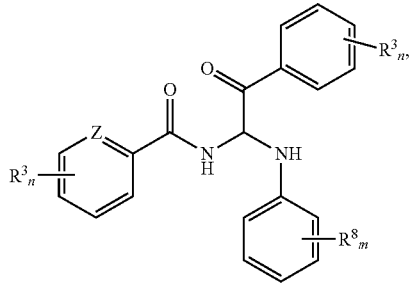

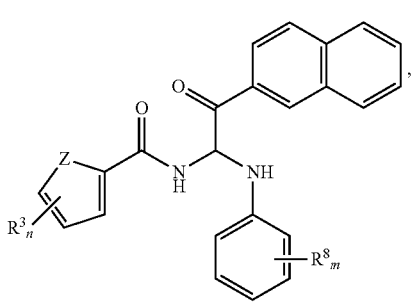

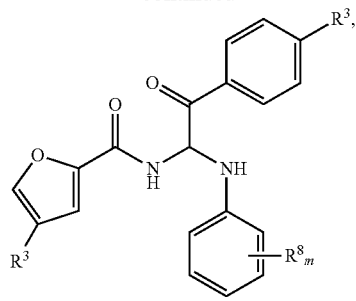

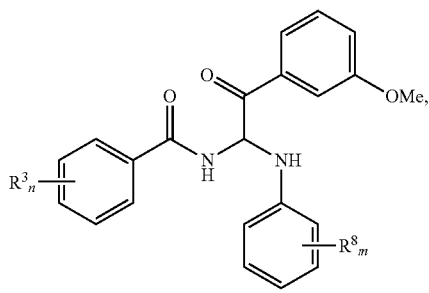

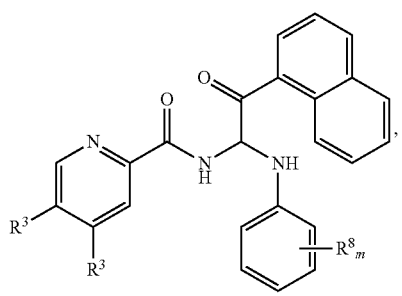

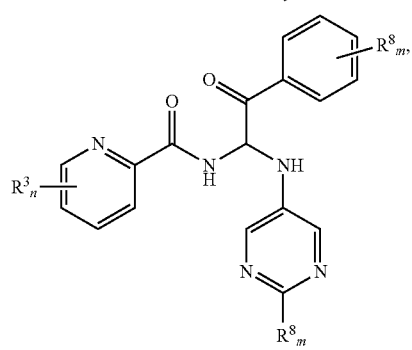

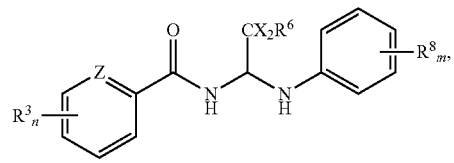

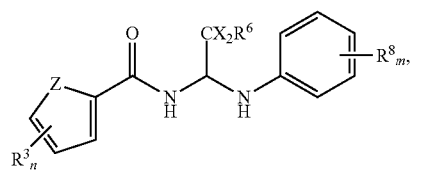

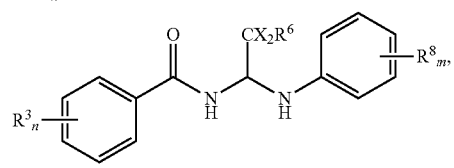

-continued
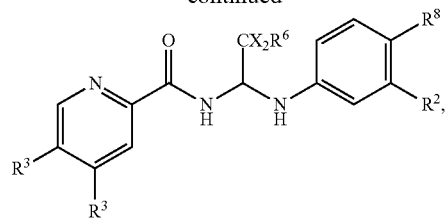
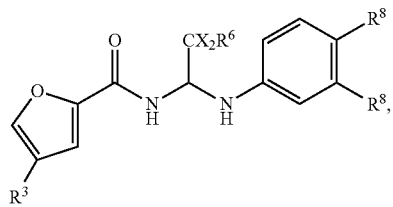
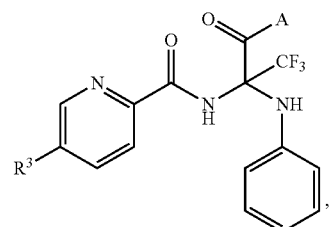
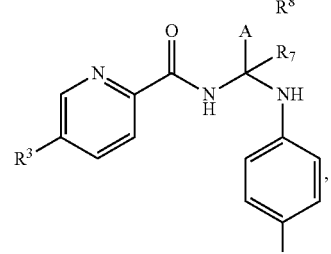
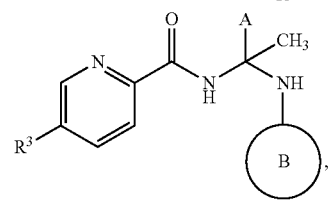
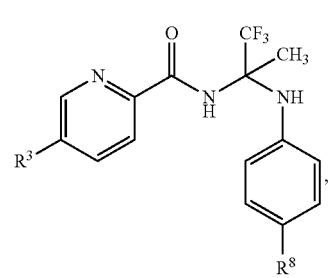
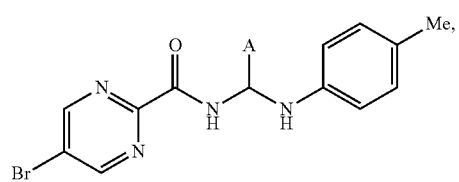
-continued
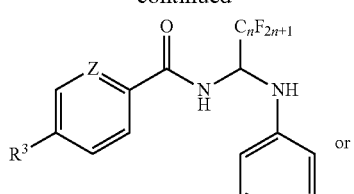
or
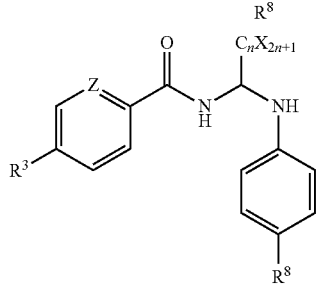
Further example compounds include:
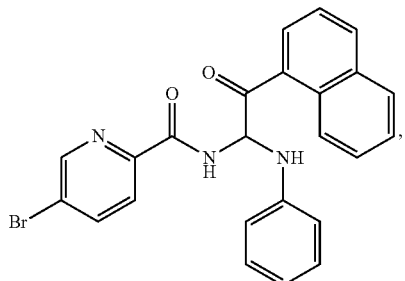
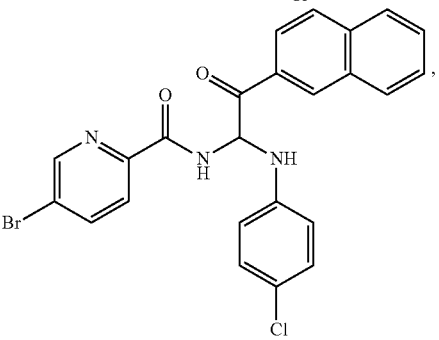
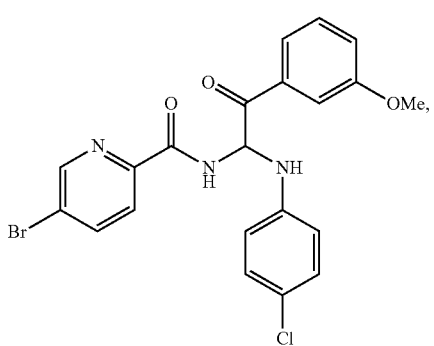

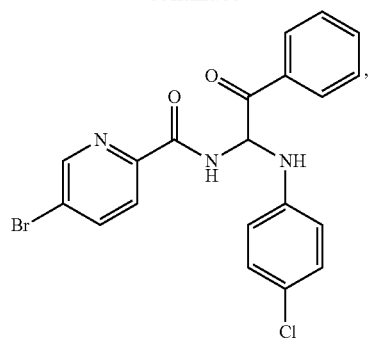
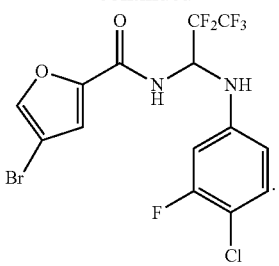
Further example compounds include
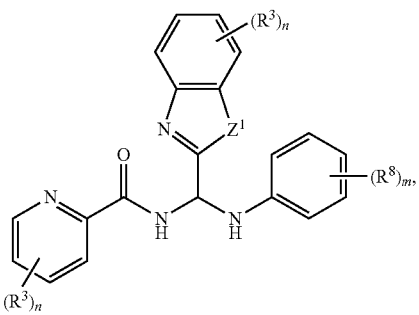
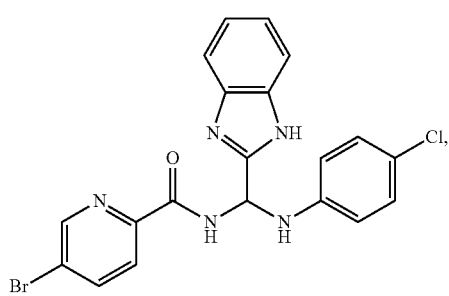
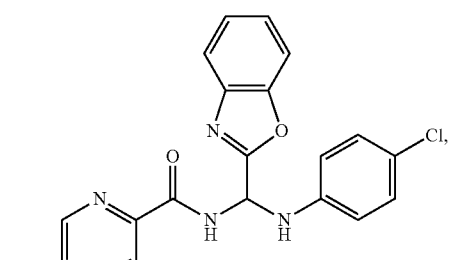
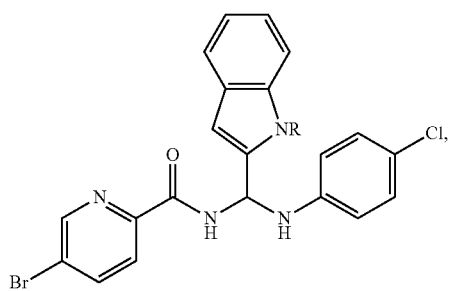

-continued

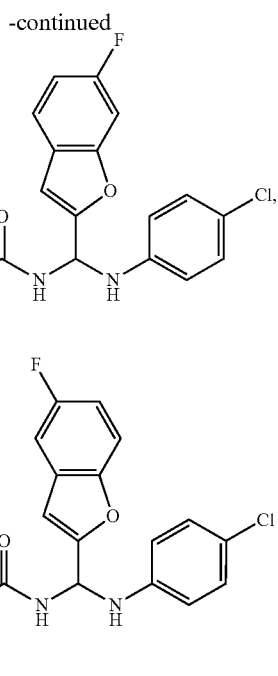

The compounds and pharmaceutical compositions described herein are useful as medicaments in mammals, including humans, for treatment of diseases and or alleviations of conditions which are responsive to treatment by antagonists of sphingosine-1-phosphate receptors. Thus, in further example embodiments, there are provided methods for treating a disorder associated with modulation of sphingosine-1-phosphate receptors. Such methods can be performed, for example, by administering to a subject in need thereof a pharmaceutical composition containing a therapeutically effective amount of at least one invention compound. The compounds described herein are useful for the treatment of mammals, including humans, with a range of conditions and diseases that are alleviated by S1P modulation such as the following conditions:

Allergies and other inflammatory diseases: Urticaria, bronchial asthma, and other airway inflammations including pulmonary emphysema and chronic obstructive pulmonary diseases;

Cardiac functions: bradycardia, congestional heart failure, cardiac arrhythmia, prevention and treatment of atherosclerosis, and ischemia/reperfusion injury;

Anti-fibrosis: ocular, cardiac, hepatic and pulmonary fibrosis, proliferative vitreoretinopathy, cicatricial pemphigoid, surgically induced fibrosis in cornea, conjunctiva and tenon; and Pains and Inflammatory diseases: Acute pain, flare-up of chronic pain, musculo-skeletal pains, visceral pain, pain associated with diabetic neuropathy, rheumatoid arthritis, chronic knee and joint pain, tendonitis, osteoarthritis, bursitis, neuropathic pains.

The compounds described herein may be administered at pharmaceutically effective dosages. Such dosages are normally the minimum dose necessary to achieve the desired therapeutic effect; in the treatment of chromic pain, this amount would be roughly that necessary to reduce the discomfort caused by the pain to tolerable levels. Generally, such doses will be in the range 1-1000 mg/day; more preferably in the range 10 to 500 mg/day. In another example embodiment, the compound or compounds may be present in a composition in a range of about 0.5 or about 1 to about 100 mg/kg/day. However, the actual amount of the compound to be administered in any given case will be determined by a physician taking into account the relevant circumstances, such as the severity of the pain, the age and weight of the patient, the patient's general physical condition, the cause of the pain, and the route of administration.

The compounds are useful in the treatment of pain in a mammal; particularly a human being. Both acute pain and chronic pain may be treated by administration of the compounds and compositions described herein. By "acute pain" is meant immediate, usually high threshold, pain brought about by injury such as a cut, crush, burn, or by chemical stimulation such as that experienced upon exposure to capsaicin, the active ingredient in chili peppers. By "chronic pain" is meant pain other than acute pain, such as, without limitation, neuropathic pain, visceral pain (including that brought about by Crohn's disease and irritable bowel syndrome (IBS)), and referred pain.

Preferably, the patient will be administered a compound orally in any acceptable form, such as a tablet, liquid, capsule, powder and the like. However, other routes may be desirable or necessary, particularly if the patient suffers from nausea. Such other routes may include, without exception, transdermal, parenteral, subcutaneous, intranasal, intrathecal, intramuscular, intravenous, and intrarectal modes of delivery. Additionally, formulations may be designed to delay release of the active compound over a given period of time, or to carefully control the amount of drug released at a given time during the course of therapy.

In another embodiment, provided are pharmaceutical compositions including at least one compound in a pharmaceutically acceptable carrier. The phrase "pharmaceutically acceptable" means the carrier, diluent or excipient must be compatible with the other ingredients of the formulation and not deleterious to the recipient thereof.

Pharmaceutical compositions can be used in the form of a solid, a solution, an emulsion, a dispersion, a micelle, a liposome, and the like, wherein the resulting composition contains one or more compounds described herein, as an active ingredient, in admixture with an organic or inorganic carrier or excipient suitable for enteral or parenteral applications. One or more compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Compounds described herein are included in pharmaceutical compositions in an amount sufficient to produce the desired effect upon the process or disease condition.

Pharmaceutical compositions may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing compounds described herein in admixture with non-toxic pharmaceutically acceptable excipients may also be manufactured by known methods.

The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin, or olive oil.

The pharmaceutical compositions may also be in the form of a sterile injectable suspension. Suspensions may be formulated according to known methods using suitable dispersing or wetting agents and suspending agents. The sterile injectable preparations may also be sterile injectable solutions or suspensions in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Compounds described herein may also be administered in the form of suppositories for rectal administration. These compositions may be prepared by mixing the compounds with a suitable non-irritating excipient, such as cocoa butter, synthetic glyceride esters of polyethylene glycols, which are solid at ordinary temperatures, but liquify and/or dissolve in the rectal cavity to release the drug.

The compounds described herein can also be administered as an ophthalmically acceptable formulation or composition. A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in ophthalmic compositions described herein include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In one example embodiment, an ophthalmic composition as described herein may have ingredients used in the following amounts listed in Table 1.

TABLE 1

| Ingredient | Amount (% w/v) |
| --- | --- |
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

Since individual subjects may present a wide variation in severity of symptoms and each composition has its unique therapeutic characteristics, the precise mode of administration and dosage employed for each subject is left to the discretion of the practitioner.

EXAMPLE 1

General Synthesis A

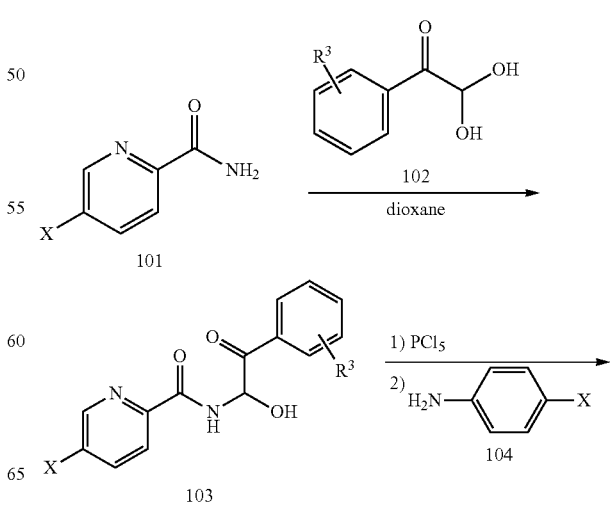

-continued

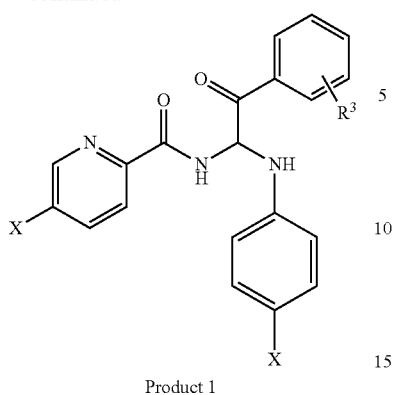

Product 1

Scheme A depicts example methods for preparation of compounds described herein. Substituted (halogenated) picolinamides 101 are reacted with substituted 2,2-dihydroxy-1-arylethanones 102 to form intermediates such as 103. Activation of 103 with a reagent such as PCl₅ precedes reaction with various anilines, such as 4-haloaniline 104, to form Product 1.

EXAMPLE 2

General Synthesis B

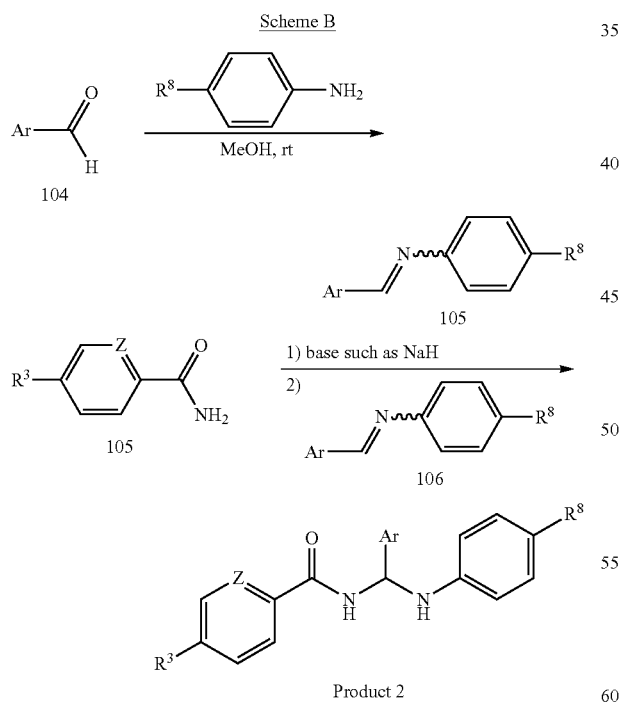

Product 2

Scheme B depicts example methods for preparation of compounds described herein. Aldehydes such as substituted aryl aldehydes or heteroaryl aldehydes 104 are condensed with substituted analines to form intermediates such as arylimine 105. Benzamines (Z=CH) or picolinamides (Z=N) 106 are treated with a base such as sodium hydride and reacted with the arylimines 105, to form Product 2.

EXAMPLE 3

General Synthesis C

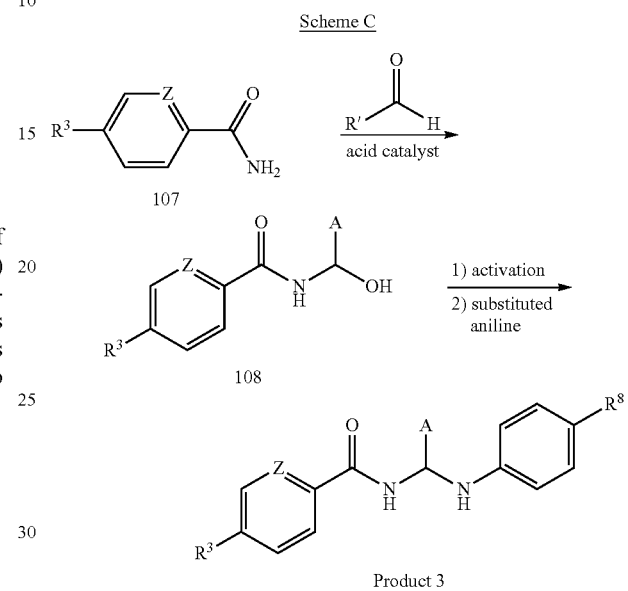

Product 3

Scheme C depicts example methods for preparation of a variety of compounds described herein. Substituted benzamines or picolinamines 107 are reacted with an aldehyde in the presence of an acid (HCl or pTsOH) to form intermediate material 108. The intermediate material 108 can be activated with an appropriate leaving group such as a halogen or a benzotraizole. This activated moiety of 108 is reacted with substituted anilines (in the presence of a base) to form Product 3.

EXAMPLE 4

General Synthesis D

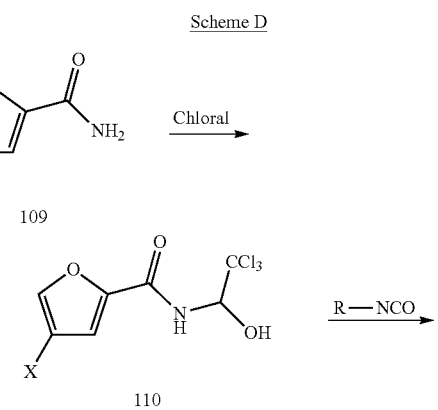

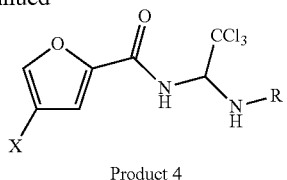

Product 4

Scheme D depicts another example method for the preparation of compounds described herein. Materials such as 4-substituted-furan-2-carboxamide 109 are reacted with chloral to produce materials such as intermediate 110. Intermediate 110 is reacted with isocyanide compounds to form Product 4.

EXAMPLE 5

Preparation of 5-bromo-N-(1-(4-chlorophenylamino)-2-(naphthalen-1-yl)-2-oxoethyl)picolinamide (Compound-1)

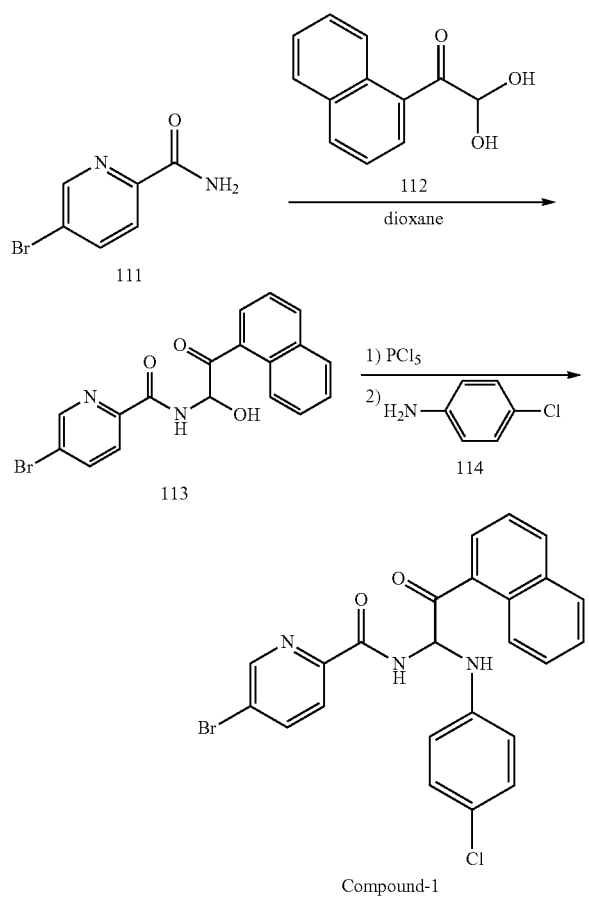

Compound-1

A mixture of 5-bromopicolinamide 111 (0.588 g, 2.92 mmol) and 2,2-dihydroxy-1-(naphthalen-1-yl)ethanone 112 (1.20 g, 5.67 mmol) in dioxane (20 mL) were heated at 100° C. for 18 hours. The dioxane was removed under vacuum and the residue was dissolved in chloroform and methanol and concentrated onto silica gel. The material was purified by auto flash system ($CH_2Cl_2$ to 1% MeOH: $CH_2Cl_2$) to give 5-bromo-N-(1-hydroxy-2-(naphthalen-1-yl)-2-oxoethyl)picolinamide 113 as a tan solid (0.74 g, 66%).

5-bromo-N-(1-hydroxy-2-(naphthalen-1-yl)-2-oxoethyl) picolinamide 113 (0.74 g, 1.93 mmol) in chloroform (20 mL) was reacted with $PCl_5$ (0.43 g, 1.96 mmol). The mixture was heated to 50° C. for 30 minutes and cooled to 0° C. 4-Chloroaniline 114 (0.512 g, 4.01 mmol) in THF (10 mL) was added and allowed to react for 1 hour. The reaction was quenched with water and the product was extracted with ethyl acetate. The organic solution was dried over $MgSO_4$, filtered and concentrated onto silica gel. The product was purified by auto flash column chromatography (30 to 50% $CH_2Cl_2$: hexane) followed by titration with diethyl ether to give 5-bromo-N-(1-(4-chlorophenylamino)-2-(naphthalen-1-yl)-2-oxoethyl)picolinamide (Compound-1, 352 mg, 37%). $^1$H NMR (300 MHz, $CDCl_3$): δ=8.83 (d, J=8.7 Hz, 1H), 8.50 (d, J=1.5 Hz, 1H), 8.46 (d, J=9.6 Hz, 1H), 8.39 (dd, J=1.2, 7.2 Hz, 1H), 8.07-8.03 (m, 2H), 7.93 (dd, J=2.4, 8.7 Hz, 1H), 7.89 (d, J=7.5 Hz, 1H), 7.68-7.63 (m, 1H), 7.56 (t, J=7.8 Hz, 2H), 7.16 (d, J=8.7 Hz, 2H), 7.09-7.03 (m, 1H), 6.82 (d, J=9.0 Hz, 2H) 5.41 (d, J=8.1 Hz, 1H).

EXAMPLE 5A-2

Use of 2,2-dihydroxy-1-(naphthalen-2-yl)ethanone in the procedure for Example A-1 produced 5-bromo-N-(1-(4-chlorophenylamino)-2-(naphthalen-2-yl)-2-oxoethyl)picolinamide (Compound-2): $^1$H NMR (300 MHz, $CDCl_3$): δ=8.87 (d, J=1.5 Hz, 1H), 8.50 (d, J=0.6, 2.4 Hz, 1H), 8.42 (d, J=9.9 Hz, 1H), 8.17 (dd, J=1.8, 8.4 Hz, 1H), 8.10 (dd, J=0.6, 8.4 Hz, 1H), 8.03 (d, J=7.8 Hz, 1H), 7.96-7.90 (m, 2H), 7.86 (d, J=8.1 Hz, 1H), 7.65-7.53 (m, 2H), 7.19-7.12 (m, 3H), 6.85 (d, J=8.7 Hz, 2H), 5.50 (brs, 1H).

EXAMPLE 5A-3

Use of 2,2-dihydroxy-1-(3-methoxyphenyl)ethanone in the procedure for Example A-1 produced 5-bromo-N-(1-(4-chlorophenylamino)-2-(3-methoxyphenyl)-2-oxoethyl)picolinamide (Compound-3): $^1$H NMR (300 MHz, $CDCl_3$): δ=8.51 (dd, J=0.9, 2.4 Hz, 1H), 8.35 (d, J=10.2 Hz, 1H), 8.09 (dd, J=0.9, 8.4 Hz, 1H), 7.96 (dd, J=2.1, 8.1 Hz, 1H), 7.84-7.81 (m, 1H), 7.74-7.73 (m, 1H), 7.40 (t, J=8.1 Hz, 1H), 7.15 (d, J=8.7 Hz, 2H), 6.96 (dd, J=8.1, 10.2 Hz, 1H), 6.80 (d, J=9.0 Hz, 2H), 5.40 (d, J=8.1 Hz, 1H).

EXAMPLE 5A-4

Use of 2,2-dihydroxy-1-phenylethanone in the procedure for Example A-1 produced 5-bromo-N-(1-(4-chlorophenylamino)-2-oxo-2-phenylethyl)picolinamide (Compound-4): $^1$H NMR (300 MHz, $CDCl_3$): δ=8.52 (dd, J=0.9, 2.1 Hz, 1H), 8.36 (d, J=9.9 Hz, 1H), 8.24-8.20 (m, 2H), 8.10 (dd, J=0.9, 8.4 Hz, 1H), 7.97 (dd, J=2.4, 8.4 Hz, 1H), 7.65-7.59 (m, 1H), 7.54-7.59 (m, 1H), 7.54-7.48 (m, 2H), 7.16 (d, J=9.0, 2H), 7.01-6.95 (m, 1H), 6.81 (d, J=9.0 Hz, 2H), 5.38 (d, J=8.1 Hz, 1H).

EXAMPLE 5A-5

Use of 1-(biphenyl-4-yl)-2,2-dihydroxyethanone in the procedure for Example A-1 produced N-(2-(biphenyl-4-yl)-1-(4-chlorophenylamino)-2-oxoethyl)-5-bromopicolinamide (Compound-5): $^1$H NMR (300 MHz, $CDCl_3$): δ=8.52 (dd, J=0.6, 2.1 Hz, 1H), 8.39 (d, J=9.9 Hz, 1H), 8.29 (d, J=9.0 Hz, 2H), 8.11 (dd, J=0.6, 8.1 Hz, 1H), 7.96 (dd, J=2.4, 8.4 hz, 1H), 7.72 (d, J=8.4 Hz, 2H), 7.62-7.59 (m, 2H), 7.49-7.40 (m, 3H), 7.16 (d, J=8.7 Hz, 2H), 7.01 (dd, J=8.4, 9.9 Hz, 1H), 6.83 (d, J=8.7 Hz, 2H).

EXAMPLE 6

Preparation of 4-bromo-N4(4-chlorophenylamino)(2,6-difluorophenyl)methyl)benzamide (Compound 6)

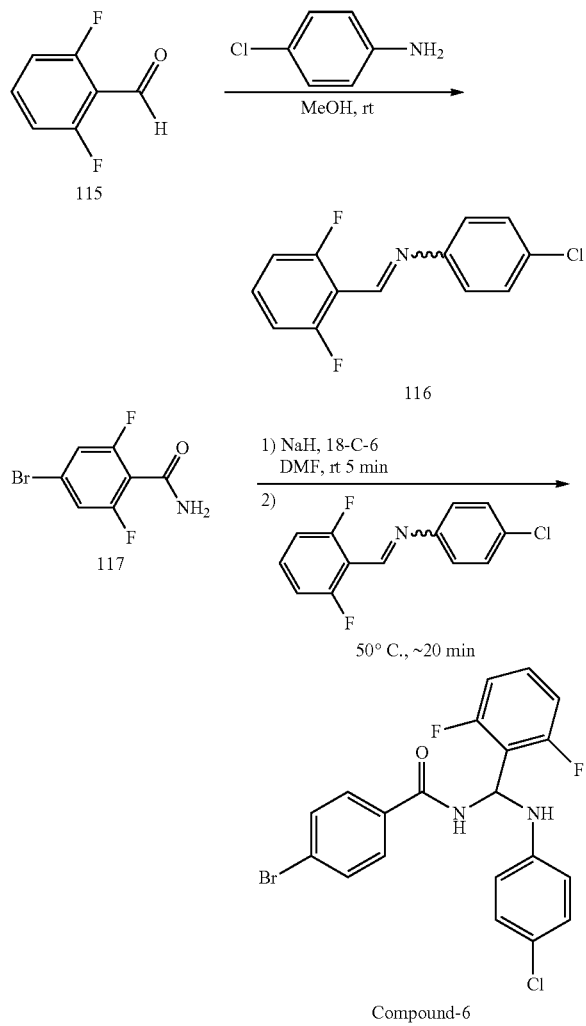

A mixture of 4-chloroaniline (1.84 g, 14.1 mmol) and 2,6-difluorobenzaldehyde 115 (1.55 mL, 14.1 mmol) in methanol (MeOH, 30 mL) was allowed to react for 18 hours at room temperature. The mixture was evaporated giving 4-chloro-N-(2,6-difluorobenzylidene)aniline 116 as a yellow solid.

4-Bromobenzamide 117 (0.94 g, 4.56 mmol) and 18-crown-6 (1.2 g, 4.54 mmol) in DMF (6 mL) was treated with sodium hydride (0.37 g, 9.25 mmol) for 5 minutes at room temperature. 4-Chloro-N-(2,6-difluorobenzylidene) aniline 116 (0.936 g, 3.72 mmol) in DMF (4 mL) was added and the mixture was heated to 50° C. for 5 minutes. The reaction mixture was quenched with crushed ice and the product was isolated by a typical aqueous workup and extraction with ethyl acetate. Chromatographic purification (9:1 hexanes:ethyl acetate) followed by trituration (ethanol) of the material gave 4-bromo-N-((4-chlorophenylamino)(2,6-difluorophenyl)methyl)benzamide (Compound-6) as a white solid (292 mg, 17%). $^1$H NMR (300 MHz, CDCl$_3$): δ=7.62-7.52 (series m, 4H), 7.38-7.28 (m, 1H), 7.19-7.15 (m, 2H), 7.14-7.08 (m, 1H), 7.02-6.96 (m, 2H), 6.88-6.85 (m, 1H), 6.76-6.72 (m, 2H).

EXAMPLE 6A-1

5-Bromo-N-((4-chlorophenyl)(4-chlorophenylamino)methyl)picolinamide (Compound-7): $^1$H NMR (300 MHz, CDCl$_3$): δ=8.57 (dd, J=2.1, 0.6 Hz, 1H), 8.36 (d, J=8.4 Hz, 1H), 8.08 (dd, J=8.1, 0.6 Hz, lH), 7.99 dd, J=8.4, 2.4 Hz, 1H), 7.50-7.46 (m, 2H), 7.40-7.36 (m, 2H), 7.15-7.11 (m, 2H), 6.69-6.65 (m, 2H), 6.57 (t, J=7.5 Hz, 1H), 4.35 (d, J=7.2 Hz, 1H).

EXAMPLE 6A-2

4-Bromo-N-((4-chlorophenylamino)(quinolin-7-yl)methyl)benzamide (Compound-8): $^1$H NMR (300 MHz, d$^6$-DMSO): δ=9.35 (t, J=3.6 Hz, 1H), 8.90 (dd, J=4.2, 1.8 Hz, 1H), 8.36 (d, J=8.1 Hz, 1H), 8.20 (s, 1H), 8.01 (d, J=8.4 Hz, 1H), 7.84 (d, J=8.7 Hz, 2H), 7.78 (dd, J=8.4, 1.5 Hz, 1H), 7.66 (d, J=8.4 Hz, 2H), 7.52 (dd, J=8.1, 4.2 Hz, 1H), 7.14 (d, J=9.0 Hz, 2H), 6.77 (d, J=9.0 Hz, 2H), 6.65 (d, J=3.6 Hz, 2H).

EXAMPLE 6A-3

5-Bromo-N-((4-chlorophenylamino)(quinolin-7-yl)methyl)picoinamide (Compound-9): $^1$H NMR (300 MHz, CDCl$_3$): δ=8.87 (dd, J=4.5, 1.8 Hz, 1H), 8.59 (d, J=8.7 Hz, 1H), 8.50 (dd, J=2.1, 0.6 Hz, 1H), 8.25 (s, 1H), 8.11 (d, J=4.2 Hz, 1H), 8.04 (dd, J=8.4, 0.5 Hz, 1H), 7.93 (dd, J=8.4, 2.1 Hz, 1H), 7.80 (d, J=8.4 Hz, 1H), 7.68 (dd, J=8.7, 1.8 Hz, 1H), 7.38 (dd, J=8.7, 2H), 6.82 (t, J=8.4 Hz, 1H), 6.72 (d, J=9.3 Hz, 2H), 4.77 (d, J=7.5 Hz, 1H).

EXAMPLE 6A-4

N-(benzofuran-2-yl(4-chlorophenylamino)methyl)-5-bromopicolinamide (Compound-10): $^1$H NMR (300 MHz, CDCl$_3$): δ=8.59 (dd, J=0.9, 2.1 Hz, 1H), 8.49 (d, J=8.7 Hz, 1H), 8.11 (dd, J=0.6, 8.4 Hz, 1H), 7.99 (dd, J=2.4, 8.1 Hz, 1H), 7.57-7.48 (m, 2H), 7.34-7.24 (m, 2H), 7.18-7.15 (m, 2H), 6.85-6.76 (m, 4H), 4.77 (d, J=8.4 Hz, 1H).

EXAMPLE 6A-5

N-(benzo[b]thiophen-2-yl(4-chlorophenylamino)methyl)-5-bromopicolinamide (Compound-11): $^1$H NMR (300 MHz, CDCl$_3$): δ=8.59 (dd, J=0.9, 2.1 Hz, 1H), 8.53 (d, J=8.7 Hz, 1H), 8.11 (dd, J=0.6, 8.4 Hz, 1H), 7.98 (dd, J=1.8, 8.1 Hz, 1H), 7.82-7.78 (m, 1H), 7.73-7.70 (m, 1H), 7.39-7.31 (m, 3H), 7.15 (d, J=8.7 Hz, 2H), 6.98-6.92 (m, 1H), 6.76 (d, J=9.0 Hz, 2H), 4.70 (d, J=8.1 Hz, 1H).

EXAMPLE 6A-6

5-bromo-N-((4-chlorophenylamino)(pyridin-3-yl)methyl)picolinamide (Compound-12): $^1$H NMR (300 MHz, CDCl$_3$): δ=8.81 (d, J=2.4 Hz, 1H), 8.60 (dd, J=1.8, 5.1 Hz, 1H), 8.56 (dd, J=0.9, 2.4 Hz, 1H), 8.44 (d, J=8.7 Hz, 1H), 8.07 (dd, J=0.9, 8.7 Hz, 1H), 7.98 (dd, J=1.8, 8.1 Hz, 1H), 7.87-7.83 (m, 1H), 7.34-7.30 (m, 1H), 7.13 (d, J=9.0 Hz, 2H), 6.71-6.63 (m, 3H), 4.51 (d, J=7.5 Hz, 1H).

EXAMPLE 6A-7

5-bromo-N-((4-chlorophenylamino)(pyridin-4-yl)methyl)picolinamide (Compound-13): $^1$H NMR (300 MHz, CDCl$_3$): δ=8.65 (dd, J=1.8, 4.8 Hz, 2H), 8.58 (dd, J=0.6, 2.1 Hz, 1H), 8.42 (d, J=8.4 Hz, 1H), 8.08 (dd, J=0.9, 8.4 Hz, 1H), 8.00 (dd, J=2.1, 8.1 Hz, 1H), 7.47-7.45 (m, 2H), 7.14 (d, J=9.0 Hz, 2H), 6.69 (t, J=8.7 Hz, 2H), 6.62 (t, J=8.4 Hz, 1H), 4.48 (d, J=7.8 Hz, 1H).

EXAMPLE 6A-8

5-bromo-N-((4-chlorophenylamino)(pyridin-2-yl)methyl)picolinamide (Compound-14): $^1$H NMR (300 MHz, CDCl$_3$): δ=8.62-8.60 (m, 1H), 8.52 (dd, J=0.6, 2.4 Hz, 1H), 8.49 (d, J=8.7 Hz, 1H), 8.10 (dd, J=0.6, 8.4 Hz, 1H), 7.96 (dd, J=2.4, 8.4 Hz, 1H), 7.75-7.69 (m, 1H), 7.54 (d, J=7.8 Hz, 1H), 7.32-7.27 (m, 1H), 7.13 (d, J=9.0 Hz, 2H), 6.77 (d, J=8.7 Hz, 2H), 6.69 (dd, J=7.5, 9.0 Hz, 1H), 5.78 (d, J=7.5 Hz, 1H).

EXAMPLE 7

Preparation of 4-bromo-N-(2,2-dichloro-1-(4-chlorophenylamino)butyl)benmide (Compound 15)

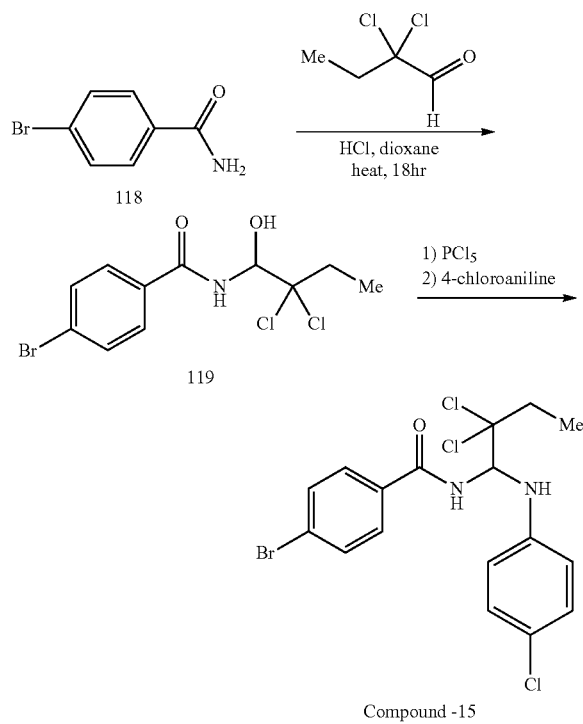

Compound-15

4-Bromobenzamide 118 (1.0 g, 4.85 mmol), 2,2-dichlorobutanal (2 mL) and HCl (3 drops) in dioxane (4 mL) were heated to 120° C. (bath temperature) for 18 hours. The mixture was concentrated, and absorbed onto silica gel. Chromatography (CH$_2$Cl$_2$) produced an off-white solid as 4-bromo-N-(2,2-dichloro-1-hydroxybutyl)benzamide 119 (0.84 g, 51%).

A solution of 4-bromo-N-(2,2-dichloro-1-hydroxybutyl)benzamide 119 (0.84 g, 2.48 mmol) in chloroform (15 mL) was reacted with PCl$_5$ (0.54 g, 2.46 mmol) at 50° C. for 30 minutes. The mixture was cooled to room temperature and quenched with ice. The aqueous layer was extracted with ether. The organic solution was dried over MgSO$_4$, filtered, and reacted with 4-chloroaniline (0.66 g, 5.17 mmol). The mixture was stirred for 18 hours at room temperature. An acidic, (HCl) aqueous workup and ether extraction preceded chromatographic purification on silica gel (7:3 hexane:CH$_2$Cl$_2$). 4-Bromo-N-(2,2-dichloro-1-(4-chlorophenylamino)butyl)benzamide (Compound-15) was obtained as a white solid (701 mg, 62%). $^1$H NMR (300 MHz, CDCl$_3$): δ=7.64-7.56 (m, 4H), 7.16 (d, J=9.0 Hz, 2H), 6.73 (d, J=8.7 Hz, 2H), 6.48 (d, J=9.6 Hz, 1H), 6.01 (d, J=9.0 Hz, 1H), 2.50-2.27 (m, 2H), 1.27 (t, J=7.2 Hz, 3H).

The following compounds were prepared according to procedures outlined in Example B.

EXAMPLE 7B-1

4-Bromo-N-(1-(4-chlorophenylamino)-2,2,3,3,3-pentafluoropropyl)benzamide (Compound-16): $^1$H NMR (300 MHz, CDCl$_3$): δ=7.71 (d, J=5.4 Hz, 2H), 7.64 (d, J=5.4 Hz, 2H), 7.15 (d, J=5.4 Hz, 2H), 6.33 (dd, J=9.3, 5.1 Hz, 1 H).

EXAMPLE 7B-2

4-Bromo-N-(2-chloro-1-(4-chlorophenylamino)-2,2-difluoroethyl)benzamid (Compound-17): $^1$H NMR (500 MHz, CD$_3$OD): δ=7.72 (d, J=5.1 Hz, 2H), 7.63 (d, J=5.4 Hz, 2H), 6.78 (d, J=5.4 Hz, 2H), 6.22 (dd, J=5.4, 4.2 Hz, 1 H).

EXAMPLE 7B-3

4-Bromo-N-(2,2-dichloro-1-(4-chlorophenylamino)ethyl)benzamide (Compound-18): $^1$H NMR (300 MHz, CD$_3$OD): δ=7.71 (d, J=8.8 Hz, 2H), 7.62 (d, J=8.7 Hz, 2H), 7.13 (d, J=8.7 Hz, 2H), 6.77 (d, J=9.3 Hz, 2H), 6.30 (d, J=3.9 Hz, 1H), 5.93 (d, J=3.9 Hz, 1H).

EXAMPLE 7B-4

4-bromo-N-(1-(4-chlorophenylamino)-2,2,3,3,4,4,5,5,6,6,7,7-dodecafluoroheptyl)benzamide (Compound-19): $^1$H NMR (300 MHz, CDCl$_3$): δ=8.53 (dd, J=2.4, 0.9 Hz, 1H), 8.24 (d, J=10.2, 1H), 8.03 (dd, J=8.4, 0.9 Hz, 1H), 7.94 (dd, J=8.7, 2.4 Hz, 1H), 7.10 (d, J=9.0 Hz, 2H), 6.68 (d, J=8.7 Hz, 2H), 6.33-6.26 (m, 1H), —CF$_2$H 5.97 (tt, J=51.9, 5.1 Hz, 1H), 4.26 (d, J=11.1 Hz, 1H).

EXAMPLE 7B-5

4-Bromo-N-(2,2-dichloro-1-(4-chlorophenylamino)ethyl)benzamide (Compound-20): $^1$H NMR (300 MHz, CD$_3$OD): δ=7.71 (d, J=8.4 Hz, 2H), 7.63 (d, J=8.4 Hz, 2H), 7.12 (d, J=9.0 Hz, 2H), 6.79 (d, J=9.0 Hz, 2H), 6.02 (d, J=10.2 Hz, 1H), 5.47 (d, J=10.2 Hz, 1H), 2.39-2.33 (m, 2H), 1.90-1.70 (m, 2H), 0.99 (t, J=7.2 Hz, 3H).

EXAMPLE 7B-6

4-Bromo-N-(2,2-dichloro-1-(4-chlorophenylamino)hexyl)benzamide (Compound-21): $^1$H NMR (300 MHz, CDCl$_3$): δ=7.62 (d, J=8.7 Hz, 2H), 7.57 (d, J=8.7 Hz, 2H), 7.16 (d, J=9.0 Hz, 2H), 6.74 (d, J=9.0 Hz, 2H), 6.50 (d, J=9.6 Hz, 1H), 6.01 (d, J=9.0 Hz, 1H), 2.44-2.24 (m, 2H), 1.83-1.62 (m, 2H), 1.42-1.30 (m, 2H), 0.92 (t, J=7.2 Hz, 3H).

EXAMPLE 7B-7

4-Bromo-N-(2,2-dichloro-1-(4-chloro-3-fluorophenylamino)hexyl)benzamide (Compound-22): $^1$H NMR (300

MHz, CDCl₃): δ=7.63-7.53 (m, 4H), 7.16 (t, 8.7 Hz, 1H), 6.65-6.51 (m, 3H), 5.98 (d, J=9.0 Hz, 1H), 4.64 (brs, 1H), 2.42-2.22 (m, 2H), 1.82-1.60 (m, 2H), 1.42-1.30 (m, 2H), 0.92 (t, J=7.2 Hz, 3H).

EXAMPLE 7B-8

4-Bromo-N-(2,2-dichloro-1-(4-chlorophenylamino)propyl)benzamide (Compound-23): $^1$H NMR (300 MHz, CDCl₃): δ=7.63 (d, J=8.7 Hz, 2H), 7.57 (d, J=8.7 Hz, 2H), 7.16 (d, J=9.0 Hz, 2H), 6.71 (d, J=9.0 Hz, 2H), 6.43 (d, J=9.0 Hz, 1H), 5.97 (d, J=9.0 Hz, 1H), 2.29 (s, 3H).

EXAMPLE 7B-9

5-Bromo-N-(1-(4-chlorophenylamino)-2,2,3,3,4,4,4-heptafluorobutyl)picolinamide (Compound-24): $^1$H NMR (300 MHz, CDCl₃): δ=8.58 (d, J=2.1 Hz, 1H), 8.32 (d, J=9.9 Hz, 1H), 8.09 (d, J=8.4 Hz, 1H), 8.00 (dd, J=8.4, 2.4 Hz, 1H), 7.16 (d, J=8.7 Hz, 2H), 6.74 (d, J=8.7 Hz, 2H), 6.42-6.28 (m, 1H), 4.35 (d, J=10.8 Hz, 1H).

EXAMPLE 7B-10

5-Bromo-N-(2,2-dichloro-1-(4-chlorophenylamino) hexyl)picolinamide (Compound-25): $^1$H NMR (300 MHz, CDCl₃): δ=8.60 (dd, J=2.4, 0.9 Hz, 1H), 8.39 (d, J=9.9 Hz, 1H), 8.10 (dd, J=8.4, 0.6 Hz, 1H), 8.00 (dd, J=8.1, 2.1 Hz, 1H), 7.14 (d, J=9.3 Hz, 2H), 6.74 (d, J=9.0 Hz, 2H).

EXAMPLE 7B-11

5-Bromo-N-(2,2-dichloro-1-(4-chlorophenylamino)phenyl)picolinamide (Compound-26): $^1$H NMR (300 MHz, CDCl₃): δ=8.60 (dd, J=2.1, 0.6 Hz, 1H), 8.39 (d, J=9.9 Hz, 1H), 8.10 (dd, J=8.7, 0.9 Hz, 1H), 8.00 (dd, J=8.4, 2.4 Hz, 1H), 7.14 (d, J=9.0 Hz, 2H), 5.97 (t, J=9.9 Hz, 1H), 4.57 (d, J=10.2 Hz, 1H), 2.41-2.22 (m, 2H), 1.89-1.69 (m, 2H), 0.97 (t, J=7.2 Hz, 3H).

EXAMPLE 7B-12

5-Bromo-N-(2,2-dichloro-1-(4-chlorophenylamino)butyl)picolinamide (Compound-27): $^1$H NMR (300 MHz, CDCl₃): δ=8.60 (dd, J=2.1, 0.6 Hz, 1H), 8.39 (d, J=9.6 Hz, 1H), 8.10 (dd, J=8.4, 0.6 Hz, 1H), 8.00 (dd, J=8.4, 2.1 Hz, 1H), 7.14 (d, J=9.0 Hz, 2H), 6.74 (d, J=8.7 Hz, 2H), 5.98 (t, J=9.9 Hz, 1H), 4.59 (d, J=9.9 Hz, 1H), 2.48-2.28 (m, 2H), 1.27 (t, J=7.5 Hz, 3H).

EXAMPLE 7B-13

5-Bromo-N-(1-(4-chlorophenylamino)-2,2,3,3,3-pentafluoropropyl)picolinamide (Compound-28): $^1$H NMR (300 MHz, CDCl₃): δ=8.57 (dd, J=2.4, 0.9 Hz, 1H), 8.31 (d, J=10.2 Hz, 1H), 8.00 (dd, J=8.4, 2.4 Hz, 1H), 7.16 (dd J=8.7 Hz, 2H), 6.74 (d, J=8.7 Hz, 2H), 6.36-6.229 (m, 1H), 4.38 (d, J=10.8 Hz, 1H).

EXAMPLE 7B-14

5-Bromo-N-(1-(4-chlorophenylamnio)-2,2,3,3,4,4,5,5,5-nonafluoropropyl)picolinamide (Compound-29): $^1$H NMR (300 MHz, CDCl₃): δ=8.59 (dd, J=2.4, 0.9 Hz, 1H), 8.32 (d, J=9.6 Hz, 1H), 8.10 (dd, J=8.4, 0.9 Hz, 1H), 8.01 (dd, J=8.7, 2.4 Hz, 1H), 7.17 (d, J=8.7 Hz, 2H), 6.75 (d, J=9.0 Hz, 2H), 6.45-6.30 (m, 1H), 4.35 (d, J=10.8 Hz, 1H).

EXAMPLE 7B-15

5-Bromo-N-(1-(4-chloro-3-fluorophenylamino)-2,2,3,3,4,4,5,5,5-nonafluoropentyl)picolinamide (Compound-30): $^1$H NMR (300 MHz, CDCl₃): δ=8.60 (dd, J=2.1, 0.6 Hz, 1H), 8.35 (d, J=10.2 Hz, 1H), 8.10 (dd, J=8.4, 0.9 Hz, 1H), 8.02 (dd, J=8.4, 2.1 Hz, 1H), 7.20 (t, J=8.4 Hz, 1H), 6.64 (dd, J=10.5, 2.7 Hz, 1H), 6.57-6.53 (m, 1H), 6.40-6.26 (m, 1H), 4.44 (d, J=10.8 Hz, 1H).

EXAMPLE 7B-16

5-Bromo-N-(1-(cycloheptylamino)-2,2,3,3,4,4,5,5,5-nonafluoropropyl)picolinamide (Compound-31): $^1$H NMR (300 MHz, CDCl₃): δ=8.27 (dd, J=2.1, 0.9 Hz, 1H), 8.12-7.99 (m, 3H), 5.70 (brs, 1H), 2.85 (brs, 1H), 1.90-1.30 (series of m, 13H).

EXAMPLE 7B-17, and 7B-18

5-Bromo-N-(1-(4-chlorophenylamino)-2,2,3,3,3-pentafluoropropyl)picolinamide (Compound-28) was separated by chiral HPLC: Chiralcell OJ-H 20% IPA(0.1% DEA)/CO₂, 100 bar; 80 mL/min, 220 nm. First eluting enantiomer (−)-5-bromo-N-(1-(4-chlorophenylamino)-2,2,3,3,3-pentafluoropropyl)picolinamide (Compound-32) [α]-119 (c=0.728 CHCl₃) (active enantiomer); second eluting enantiomer (+)-enantiomer (Compound-33): $^1$H NMR (300 MHz, CDCl₃): δ=same as for the racemate Compound-28, Example B-13.

EXAMPLE 7B-19

5-Bromo-N-(1-(4-chloro-3-fluorophenylamino)-2,2,3,3,3-pentafluoropropyl)picolinamide (Compound-34) $^1$H NMR (300 MHz, CDCl₃) δ=8.56 (dd, J=0.6, 2.1 Hz, 1H), 8.37 (d, J=9.6 Hz, 1H), 8.09 (dd, J=0.6, 8.1 Hz, 1H), 8.00 (dd, J=2.1, 8.1 Hz, 1H), 7.17 (t, J=8.7 Hz, 1H), 6.63 (dd, J=2.4, 10.8 Hz, 1H), 6.56-6.52 (m, 1H), 6.33-6.19 9m, 1H), 4.55 (d, J=10.5 Hz, 1H).

EXAMPLE 7B-20

5-Bromo-N-(1-(2-chloropyrimidin-5-ylamino)-2,2,3,3,3-pentafluoropropyl)picolinamide (Compound-35) $^1$H NMR (300 MHz, CDCl₃) δ=8.61 (dd, J=0.9, 2.4 Hz), 8.43 (d, J=9.9 Hz, 1H), 8.27 (s, 2H), 8.09 (dd, J=2.1, 8.1 Hz, 1H), 6.35-6.20 (m, 1H), 4.52 (d, J=10.8 Hz, 1H).

EXAMPLE 7B-21

5-Bromo-N-(1-(2,6-dichloropyridin-4-ylamino)-2,2,3,3,4,4,4-heptafluorobutyl)picolinamide (Compound-36) $^1$H NMR (300 MHz, CDCl₃) δ=8.62 (dd, J=0.6, 2.1 Hz, 1H), 8.49 (d, J=9.9 Hz, 1H), 8.13 (dd, J=0.9, 8.1 Hz, 1H), 8.05 (dd, J=2.1, 8.1 Hz, 1H), 6.72 (s, 2H), 6.44-6.30 (m, 1H), 5.14 (d, J=9.9 Hz, 1H).

EXAMPLE 7B-22

5-Bromo-N-(1-(2-chloropyrimidin-5-ylamino)-2,2,3,3,4,4,5,5,6,6,7,7-dodecafluoroheptyl)picolinamide (Compound-37) $^1$H NMR (300 MHz, CDCl₃) δ=8.62 (dd, J=0.9, 2.1 Hz, 1H), 8.45 (d, J=8.3 Hz, 1H), 8.27 (s, 2H), 8.09 (dd, J=0.9, 8.4

Hz, 1H), 8.04 (dd, J=2.1, 8.1 Hz, 1H), 6.42-6.28 (m, 1H), 6.23-5.85 (m, 1H), 4.48 (d, J=10.8 Hz, 1H).

EXAMPLE 8

Preparation of 4-bromo-N-(1-(4-chlorophenylamino)-2,2-dimethylpropyl)benzamide (Compound-38)

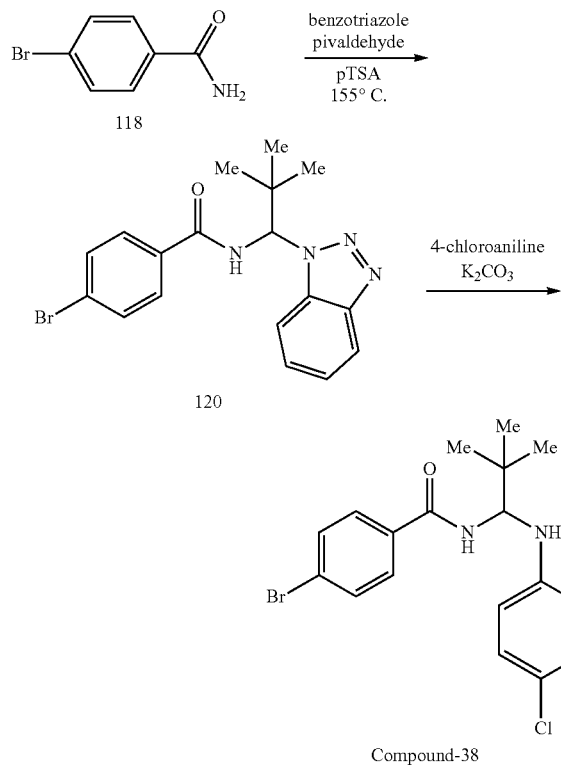

Compound-38

A mixture of 4-bromobenzamide 118 (0.73 g, 3.54 mmol), benzotriazole (0.42 g, 3.52 mmol), pivaldehyde (0.8 mL, 7.27 mmol) and pTSA-HOH (about 60 mg) was heated at reflux for 5 hours in a Dean-Stark apparatus. The mixture was concentrated onto silica gel and purified by chromatography (8:2 CH$_2$Cl$_2$:hexanes to CH$_2$Cl$_2$) to give N-(1-(1H-benzo[d][1,2,3]triazol-1-yl)-2,2-dimethylpropyl)-4-bromobenzamide 120 as a white solid.

A mixture of N-(1-(1H-benzo[d][1,2,3]triazol-1-yl)-2,2-dimethylpropyl)-4-bromobenzamide 120 as a white solid (2.38 mmol), 4-chloroaniline (0.64 g, 5.0 mmol), and K$_2$CO$_3$ (1 g, 7.23 mmol) in methanol (20 mL) and THF (2 mL) was stirred for 18 h at room temperature. The reaction was quenched with 2M HCl and extracted with ether. The organic solution was concentrated onto silica gel and chromatography (9:1 hexanes:ethyl acetate) and gave 4-bromo-N-(1-methoxy-2,2-dimethylpropyl)benzamide and the title product. The product was titrated with ether to give pure 4-bromo-N-(1-(4-chlorophenylamino)-2,2-dimethylpropyl) benzamide (Compound-38) (104 mg, 11%). $^1$H NMR (300 MHz, d$^6$-DMSO): δ=8.34 (d, J=8.4 Hz, 1H), 7.76 (d, J=8.4 Hz, 2H), 7.64 (d, J=8.4 Hz, 2H), 7.07 (d, J=8.7 Hz, 2H), 6.71 (J=8.7 Hz, 2H), 5.81 (d, J=6.6 Hz, 1H), 5.19 (t, J=3.9 Hz, 1H), 1.03 (s, 9H).

EXAMPLE 8C-1

4-Bromo-N-((4-chlorophenylamino)(phenyl)methyl)benzamide (Compound-39): $^1$H NMR (300 MHz, d$^6$-acetone): δ=8.44 (d, J=8.1 Hz, 1H), 7.86 (d, J=8.4 Hz, 2H), 7.65-7.62 (m, 4H), 7.43-7.28 (m, 3H), 7.14 (d, J=9.0 Hz, 2H), 6.85 (d, J=9.0 Hz, 2H), 6.85 (d, J=9.0 Hz, 2H), 6.70-6.64 (9m, 2H).

EXAMPLE 8C-2

4-Bromo-N-((4-chloro-3-fluorophenylamino)(cyclohexyl)methyl)benzamide (Compound-40): $^1$H NMR (300 MHz, d$^6$-DMSO): δ=8.55 (d, J=8.4 Hz, 1H), 7.76 (d, J=8.7 Hz, 2H), 7.63 (d, J=8.4 Hz, 2H), 7.15 (t, J=8.7 Hz, 1H), 6.61 (dd, J=12.9, 2.7 Hz, 1H), 6.51 (dd, J=8.7, 2.1 Hz, 1H), 6.43 (brs, 1H), 5.10-5.00 (m, 1H), 1.95 (d, J=12.6 Hz, 1H), 1.80-1.56 9m, 5H), 1.23-1.00 (m, 5H).

EXAMPLE 8C-3

4-Bromo-N-((4-chlorophenylamino)(cyclohexyl)methyl)benzamide (Compound-41): $^1$H NMR (300 MHz, CDCl$_3$): δ=7.59-7.51 (m, 4H), 7.10 (d, J=9.0 Hz, 2H), 6.62 (d, J=8.7 Hz, 2H), 6.05 (d, J=8.4 Hz, 1H), 5.37 (dd, J=8.4, 6.3 Hz, 1H), 1.96-1.66 (m, 6H), 1.33-1.13 (m, 6H).

EXAMPLE 9

Preparation of 4-bromo-N-(2,2,2-trichloro-1-(6-chloropyridin-3-ylamino)ethyl)benzamide (Compound-42)

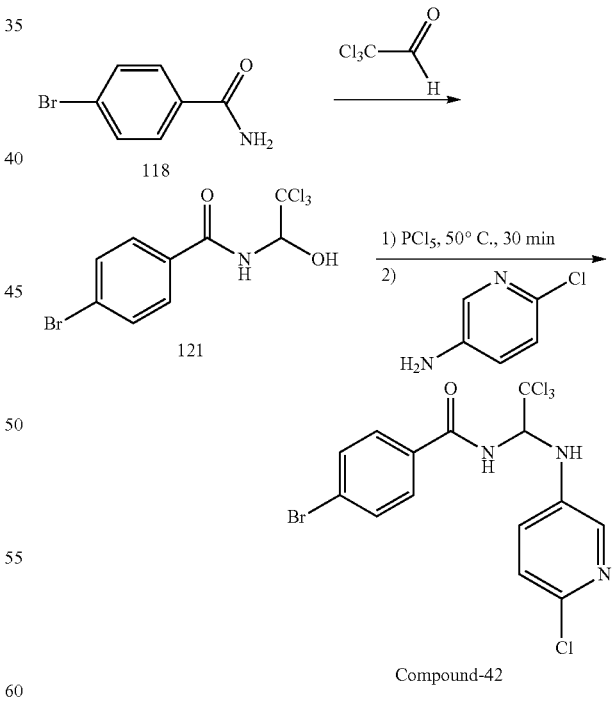

Compound-42

A mixture of 4-bromoaniline 118 (5.0 g, 24.2 mmol) and chloral (4.7 mL, 48.2 mmol) in THF (4 mL) was heated for 30 minutes. Solvent was removed under vacuum. 4-Bromo-N-(2,2,2-trichloro-1-hydroxyethyl)benzamide 121 (1.26 g, 3.62 mmol) in chloroform (15 mL) and PCl$_5$ (0.8 g, 3.65 mmol) was heated at 50° C. for 30 minutes. The product was isolated from a standard aqueous work-up and extraction to produce 4-bromo-N-(1,2,2,2-tetrachloroethyl)benzamide. 4-Bromo-N-(1,2,2,2-tetrachloroethyl)benzamide (1.21 mmol) in ether (50 mL) was reacted with 6-chloropyridin-3-amine (0.32 g, 2.44 mmol) at room temperature for 18 hours. The mixture was subjected to a standard aqueous work-up and extraction. Chromatography on silica gel (7:3 hexanes:CH$_2$Cl$_2$) gave 4-bromo-N-(2,2,2-trichloro-1-(6-chloropyridin-3-ylamino)ethyl)benzamide (Compound-42, 0.36 g, 65%). $^1$H NMR (300 MHz, d$^4$-methanol): δ=7.99 (dd, J=3.0, 0.6 Hz, 1H), 7.74 (d, J=9.0 Hz, 2H), 7.65 (d, J=9.0 Hz, 2H), 7.36 (dd, J=9.0, 3.3 Hz, 1H), 7.26 (dd, J=8.7, 0.6 Hz, 1H), 6.36 (s, 1H).

EXAMPLE 9D-1

4-Bromo-N-(2,2,2-trichloro-1-(5-chloropyrimidin-2-ylamino)ethyl)benzamide (Compound-43): $^1$H NMR (300 MHz, d$^4$-methanol): δ=8.40 (s, 2H), 7.76 (d, J=8.7 Hz, 2H), 7.67 (d, J=9.0 Hz, 2H), 7.23 (s, 1H).

EXAMPLE 9D-2

4-Bromo-N-(2,2,2-trichloro-1-(5-chloropyrazin-2-ylamino)ethyl)benzamide (Compound-44): $^1$H NMR (300 MHz, d$^4$-methanol): δ=8.20 (d, J=1.5 Hz, 1H), 7.96 (d, J=1.5 Hz, 1H), 7.74 (d, J=9.0 Hz, 2H), 7.65 (d, J=9.0 Hz, 2H), 7.17 (s, 1H).

EXAMPLE 9D-3

4-Bromo-N-(2,2,2-tribromo-1-(cyclohex-3-enylamino)ethyl)benzamide (Compound-45): 2$^{nd}$ eluting diastereomer $^1$H NMR (300 MHz, CDCl$_3$): δ=7.67-7.55 (series of m, 4H), 6.58-6.54 (m, 1H), 5.97 (d, J=2.4 Hz, 1H), 5.66-5.55 (m, 1H), 5.28-5.23 (m, 1H), 3.03-2.94 (m, 1H), 2.46-1.42 (series of m, 7H).

EXAMPLE 10

Preparation of 5-bromo-N-(2,2,2-trichloro-1-(4-ethylcycloheylamino)ethyl)picolinamide (Compound-46) and 5-bromo-N-(2,2,2-trichloro-1-(4-ethylcyclohexylamino)ethyl)picolinamide (Compound-47)

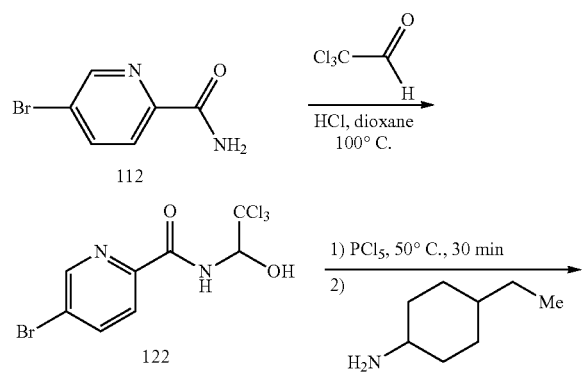

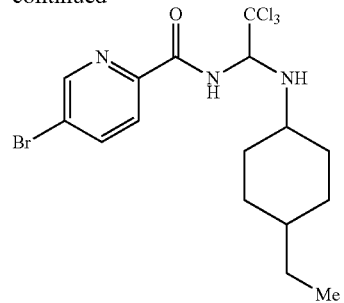

Compound-46 and 47

5-Bromopicolinamide 112 (1.29 g, 6.4 mmol) and chloral (1.25 mL) in dioxane (10 mL) were heated to 100° C. The mixture was concentrated to give 5-bromo-N-(2,2,2-trichloro-1-hydroxyethyl)picolinamide 122 (99%).

A solution of 5-bromo-N-(2,2,2-trichloro-1-hydroxyethyl)picolinamide 122 (0.83 g, 2.39 mmol) in chloroform (20 mL) was reacted with PCl$_5$ (0.51 g, 2.33 mmol) at 50° C. for 30 minutes. The mixture was cooled to −78° C. and 4-ethylcyclohexanamine was added (1 g, 7.5 mmol). After 1 hour, the mixture was warmed to room temperature. The reaction mixture was subjected to an aqueous work-up and the product extracted with chloroform. The organic solution was concentrated onto silica gel and the product was eluted (flash: 97:3 hexane:ether then prep-HPLC: Phenomenex Luna column (SiO$_2$), 10 micron, 250×50 mm, 150 mL/minute; 3:7 hexanes:dichloromethane) to give first eluting fraction: 5-bromo-N-(2,2,2-trichloro-1-(4-ethylcyclohexylamino)ethyl)picolinamide (Compound-46, 106 mg) $^1$H NMR (300 MHz, CDCl$_3$): δ=8.64 (dd, J=2.1, 0.6 Hz, 1H), 8.26 (d, J=9.9 Hz, 1H), 8.11 (dd, J=8.4, 0.6 Hz, 1H), 8.01 (dd, J=8.4, 2.4 Hz, 1H), 5.56 (t, J=9.3 Hz, 1H), 2.96 (brs, 1H), 1.80-1.71 (m, 2H), 1.59-1.21 (m, 10H), 0.85 (t, J=7.2 Hz, 3H), and second eluting fraction: 5-bromo-N-(2,2,2-trichloro-1-(4-ethylcyclohexylamino)ethyl)picolinamide (Compound-47, 166 mg) $^1$H NMR (300 MHz, CDCl$_3$): δ=8.64 (dd, J=2.1, 0.6 Hz, 1H), 8.30 (d, J=9.9 Hz, 1H), 8.11 (dd, J=8.4, 0.9 Hz, 1H), 8.01 (dd, J=8.4, 2.1 Hz, 1H), 5.50 (t, J=8.7 Hz, 1H), 2.68-2.58 (m, 1H), 2.16-2.07 (m, 1H), 1.86-1.70 (m, 4H), 1.27-1.01 (m, 6H), 0.96-0.087 (m, 1H) 0.83 (t, J=7.5 Hz, 3H).

EXAMPLE 10E-1

MPLC separation with 9:1 hexanes:ether and 8:2 then 7:3 hexanes:dichloromethane. Single diastereomer: first eluting fraction: 5-bromo-N-(2,2,2-trichloro-1-(4-methylcyclohexylamino)ethyl)picolinamide (Compound-48): $^1$H NMR (300 MHz, CDCl$_3$): δ=8.65-8.64 (m, 1H), 8.27 (d, J=9.9 Hz, 1H), 8.12-8.09 (m, 1H), 8.02-7.99 (m, 1H), 5.56 (t, J=9.3 Hz, 1H), 2.94 (brs, 1H), 1.81-1.71 (m, 2H), 1.60-1.25 (m, 8H), 0.89 (d, J=6.0 Hz, 3H).

EXAMPLE 10E-2

MPLC separation with 3 to 6% ether in hexanes gave products. First eluting diastereomer: "cis" compound, 4-bromo-N-(2,2,2-trichloro-1-(4-methylcyclohexylamino)ethyl)benzamide (Compound-49): $^1$H NMR (300 MHz, CDCl$_3$): δ=7.67 (d, J=8.7 Hz, 2H), 7.85 (d, J=8.7 Hz, 2H), 6.51 (d, J=9.3 Hz, 1H), 5.61 (d, J=9.3 Hz, 1H), 2.98-2.95 (m, 1H), 1.80-1.74 (m, 2H), 1.59-1.26 (m, 8H), 0.90 (d, J=6.0 Hz, 3H). Second eluting diastereomer: "trans" compound, 4-bromo-N-(2,2,2-trichloro-1-(4-methylcyclohexylamino)

ethyl)benzamide (Compound-50): ¹H NMR (300 MHz, CDCl₃): δ=7.68 (d, J=8.7 Hz, 2H), 7.58 (d, J=8.7 Hz, 2H), 6.61 (d, J=9.3 Hz, 1H), 5.66 (d, J=9.0 Hz, 1H), 2.67-2.58 (m, 1H), 2.12-2.05 (m, 1H), 1.90-1.60 (m, 4H), 1.37-0.90 (m, 8H), 0.86 (d, J=6.3 Hz, 3H).

EXAMPLE 11

Preparation of 4-bromo-N-(2,2,2-trichloro-1-(cyclooctylamino)ethyl)furan-2-carboxamide (Compound-51)

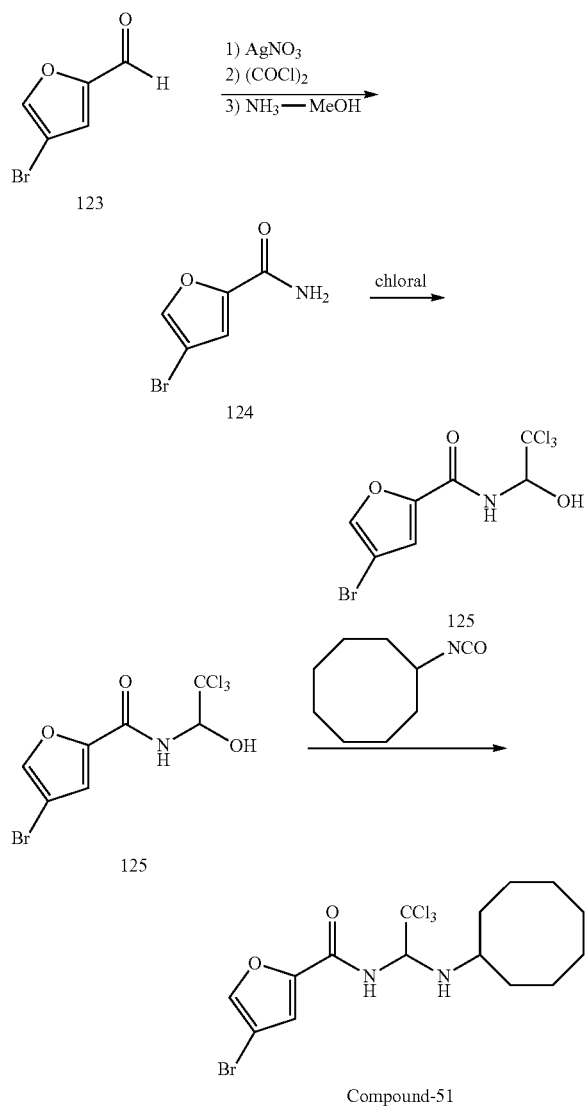

A mixture of 4-bromofuran-2-carbaldehyde 123 (1.75 g, 10 mmol) in ethanol (15 mL) and AgNO₃ (3.06 g, 20 mmol) in water (5 mL) was treated (drop-wise addition) with sodium hydroxide (1.2 g in 5 mL HOH) at room temperature for 20 minutes. The mixture was subjected to an aqueous, acidic (HCl) work-up and extraction with ether. The solvents were removed under vacuum. 4-Bromofuran-2-carboxylic acid (1.9 g) in CH₂Cl₂ was treated with oxalyl chloride (6.5 mL, 2M in CH₂Cl₂) and DMF (a few drops) for a couple hours. The solvents were removed under vacuum and replaced with benzene. The organic layer was decanted and solvent removed under reduced pressure. 4-Bromofuran-2-carbonyl chloride was dissolved in CH₂Cl₂ and cooled to -70° C. before addition of NH₃ (3 mL, ~7M solution in methanol). 4-Bromofuran-2-carboxamide 124 was recrystallized from hexanes-ethyl acetate.

A mixture of 4-bromofuran-2-carboxamide 124 (0.85 g, 4.47 mmol) and chloral (0.78 mL) in xylene was heated at 95° C. for 1.5 hours. The mixture was concentrated to give 4-bromo-N-(2,2,2-trichloro-1-hydroxyethyl)furan-2-carboxamide 125 as a tan solid that was used without further purification.

4-Bromo-N-(2,2,2-trichloro-1-hydroxyethyl)furan-2-carboxamide 125 (0.16 g, 0.47 mmol) and isocyanatocyclooctane (0.08 mL, 0.51 mmol) in benzene (2 mL) with triethyl amine (2 drops) was heated to 95° C. for 1.5 hours. The mixture was concentrated onto silica gel and purified by chromatography (7:3 to 6:4 hexane:CH₂Cl₂) to give 4-bromo-N-(2,2,2-trichloro-1-(cyclooctylamino)ethyl)furan-2-carboxamide (Compound-51) (142 mg, 67%). ¹H NMR (300 MHz, CDCl₃): δ=7.50 (d, J=0.9 Hz, 1H), 7.21 (d, J=0.9 Hz, 1H), 6.59 (d, J=9.6 Hz, 1H), 5.55 (t, J=9.3 Hz, 1H), 2.96-2.85 (m, 1H), 1.79-1.42 (m, 15H).

EXAMPLE 11F-1

4-Bromo-N-(2,2,2-trichloro-1-(cycloheptylamino)ethyl)furan-2-carboxamide (Compound-52): ¹H NMR (300 MHz, CDCl₃): δ=7.50 (d, J=0.9 Hz, 1H), 7.22 (d, J=0.9 Hz, 1H), 6.59 (d, J=9.6 Hz, 1H), 5.55 (t, J=8.7 Hz, 1H), 2.92-2.89 (m, 1H), 1.91-1.77 (m, 2H), 1.71-1.63 (m, 3H) 1.60-1.39 (m, 8H).

EXAMPLE 11F-2

4-Bromo-N-(2,2,2-trichloro-1-(cyclohexylamino)ethyl)furan-2-carboxamide (Compound-53): ¹H NMR (300 MHz, CDCl₃): δ=7.50 (d, J=0.9 Hz, 1H), 7.22 (d, J=0.6 Hz, 1H), 6.61 (d, J=9.6 Hz, 1H), 5.62-5.57 (m, 1H), 2.69 (brs, 1H), 2.02-1.99 (m, 1H), 1.82-1.69 (m, 4H), 1.62-1.52 (m, 1H), 1.30-1.13 (m, 5H).

EXAMPLE 12

In Vitro Activity

A Novel compounds with this structure were synthesized and tested for S1P3 activity using the Flipr assay. These compounds may be assessed for their ability to activate or block activation of the human S1P3 receptor in T24 cells stably expressing the human S1P3 receptor.

Ten thousand cells/wells are plated into 384-well poly-D-lysine coated plates one day prior to use. The growth media for the S1P3 receptor expressing cell line is McCoy's 5A medium supplemented with 10% charcoal-treated fetal bovine serum (FBS), 1% antibiotic-antimycotic and 400 μg/ml geneticin. On the day of the experiment, the cells are washed twice with Hank's Balanced Salt Solution supplemented with 20 mM HEPES (HBSS/Hepes buffer). The cells are then dye loaded with 2 μM Fluo-4 diluted in the HBSS/Hepes buffer with 1.25 mM Probenecid and incubated at 37° C. for 40 minutes. Extracellular dye is removed by washing the cell plates four times prior to placing the plates in the FLIPR (Fluorometric Imaging Plate Reader, Molecular Devices). Ligands are diluted in HBSS/Hepes buffer and prepared in 384-well microplates. The positive control, Sphingosine-1-phosphate (S1P), is diluted in HBSS/Hepes buffer with 4 mg/ml fatty acid free bovine serum albumin. The FLIPR transfers 12.5 μl from the ligand microplate to the cell plate and takes fluorescent measurements for 75 seconds, taking readings every second, and then for 2.5 minutes, taking readings every 10 seconds. Drugs are tested over the concentration range of 0.61 nM to 10,000 nM. Data for $Ca^{2+}$ responses are obtained in arbitrary fluorescence units and not translated into $Ca^{2+}$ concentrations. $IC_{50}$ values are determined through a linear regression analysis using the Levenburg Marquardt algorithm.

B. Novel compounds were synthesized and tested for S1P3 activity using the GTP $\gamma^{35}$S binding assay. GTP $\gamma^{35}$S binding was measured in the medium containing (mM) HEPES 25, pH 7.4, $MgCl_2$ 10, NaCl 100, dithiothreitol 0.5, digitonin 0.003%, 0.2 nM GTP $\gamma^{35}$S, and 5 μg membrane protein in a volume of 150 μl. Test compounds were included in the concentration range from 0.08 to 5,000 nM unless indicated otherwise. Membranes were incubated with 100 μM 5'-adenylylimmidodiphosphate for 30 min, and subsequently with 10 μM GDP for 10 min on ice. Drug solutions and membrane were mixed, and then reactions were initiated by adding GTP $\gamma^{35}$S and continued for 30 min at 25° C. Reaction mixtures were filtered over Whatman GF/B filters under vacuum, and washed three times with 3 mL of ice-cold buffer (HEPES 25, pH7.4, $MgCl_2$ 10 and NaCl 100). Filters were dried and mixed with scintillant, and counted for $^{35}$S activity using a β-counter. Agonist-induced GTP $\gamma^{35}$S binding was obtained by subtracting that in the absence of agonist. Binding data were analyzed using a non-linear regression method. In case of antagonist assay, the reaction mixture contained 10 nM S1P in the presence of test antagonist at concentrations ranging from 0.08 to 5000 nM.

Resulting data is shown in Table 2

TABLE 2

Activity potency at S1P3 receptor: assay GTP $\gamma^{35}$S, $IC_{50}$ nM.

| Compound Number | Structure | S1P3 GTPγ$^{35}$S IC50 nM |
|---|---|---|
| Compound-1 | 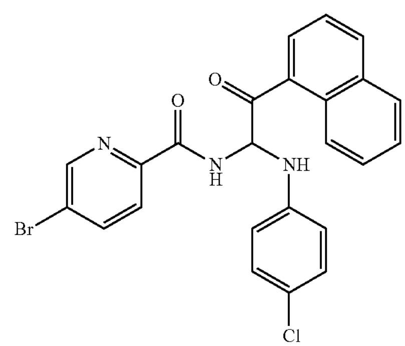 | 10 |
| Compound-2 | 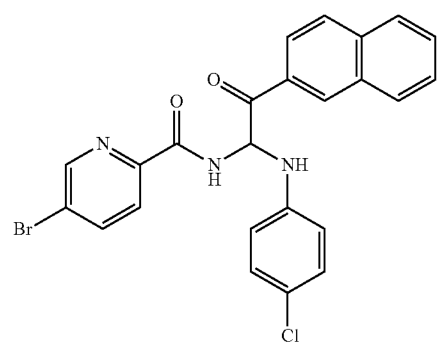 | 31 |
| Compound-3 | 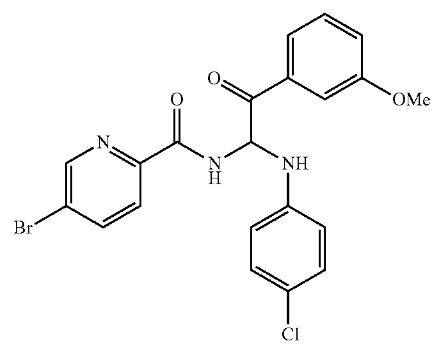 | 5.2 |

TABLE 2-continued

Activity potency at S1P3 receptor: assay GTP $\gamma^{35}$S, IC$_{50}$ nM.

| Compound Number | Structure | S1P3 GTPγ$^{35}$S IC50 nM |
|---|---|---|
| Compound-29 | 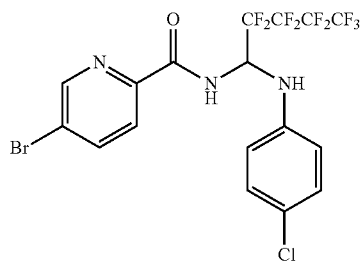 | 5.5 |
| Compound-32 | 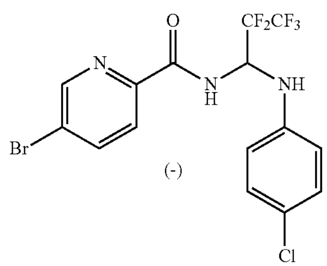 | 1.3 |
| Compound-7 | 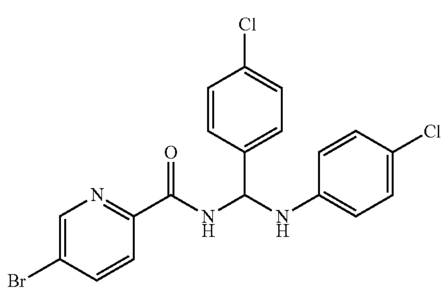 | 115 |
| Compound-27 | 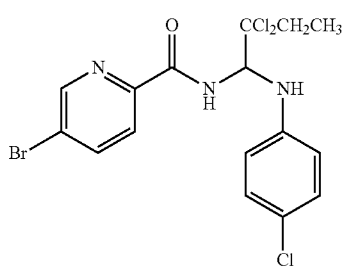 | 56 |
| Compound-49 | 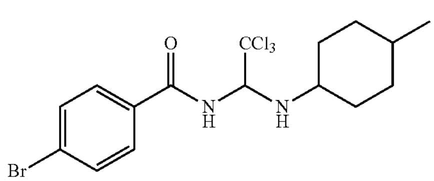 | 671 |

TABLE 2-continued

Activity potency at S1P3 receptor: assay GTP $\gamma^{35}$S, IC$_{50}$ nM.

| Compound Number | Structure | S1P3 GTP$\gamma^{35}$S IC50 nM |
|---|---|---|
| Compound-10 | 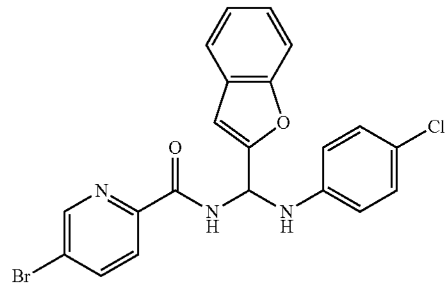 | 4.7 |
| Compound-37 | 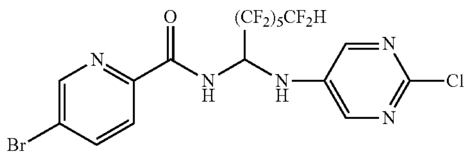 | 59 |
| Compound-35 | 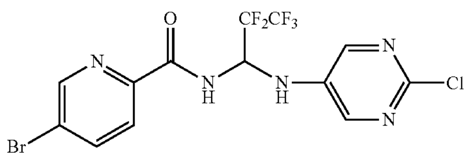 | 2 |

EXAMPLE 13

Treating Pain

I. A patient exhibits moderate pain after a bowel surgery. A tablet including 5-bromo-N-(1-(4-chlorophenylamino)-2-(naphthalen-1-yl)-2-oxoethyl)picolinamide is delivered taken by the patient twice daily as needed for the pain. The patient reports a reduction of pain when taking the tablet.

II. A patient exhibits moderate pain after a bowel surgery. A tablet including 4-bromo-N-((4-chlorophenylamino)(2,6-difluorophenyl)methyl)benzamide is delivered taken by the patient twice daily as needed for the pain. The patient reports a reduction of pain when taking the tablet.

III. A patient exhibits moderate pain after a bowel surgery. A tablet including 4-bromo-N-(2,2-dichloro-1-(4-chlorophenylamino)butyl)benmide is delivered taken by the patient twice daily as needed for the pain. The patient reports a reduction of pain when taking the tablet.

IV. A patient exhibits moderate pain after a bowel surgery. A tablet including 4-bromo-N-(1-(4-chlorophenylamino)-2,2-dimethylpropyl)benzamide is delivered taken by the patient twice daily as needed for the pain. The patient reports a reduction of pain when taking the tablet.

V. A patient exhibits moderate pain after a bowel surgery. A tablet including 4-bromo-N-(2,2,2-trichloro-1-(6-chloropyridin-3-ylamino)ethyl)benzamide is delivered taken by the patient twice daily as needed for the pain. The patient reports a reduction of pain when taking the tablet.

VI. A patient exhibits moderate pain after a bowel surgery. A tablet including 5-bromo-N-(2,2,2-trichloro-1-(4-ethylcyloheylamino)ethyl)picolinamide is delivered taken by the patient twice daily as needed for the pain. The patient reports a reduction of pain when taking the tablet.

VII. A patient exhibits moderate pain after a bowel surgery. A tablet including 5-bromo-N-(2,2,2-trichloro-1-(4-ethylcyclohexylamino)ethyl)picolinamide is delivered taken by the patient twice daily as needed for the pain. The patient reports a reduction of pain when taking the tablet.

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, and formulation.

The structures depicted and described herein are intended to include every possible stereoisomer, both pure or in any possible mixture.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A compound having a structure

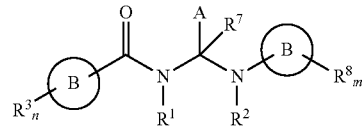

wherein $R^1$ and $R^2$ are each independently selected from H, $C_1$-$C_4$ alkyl;

C is a phenyl, aryl or heteroaryl, having a structure

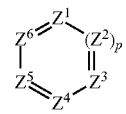

and p is 0-1 and $Z^1$-$Z^6$ are each independently selected from C, N, O and S;

$R^3$ and $R^8$ are each independently selected from H, $C_1$-$C_6$ straight or branched chain alkyl, alkenyl, or alkynyl, alkoxy (such as $O(C_1$-$C_6))$, —OH, halogen, —$NR^4_2$, —CN, —$CO_2R^4$, —C(O)$NR^4R^5$, —$CH_2OH$, —$CF_3$, —$OCHF_2$, —$OCF_3$, —$NO_2$, alkylamino, and alkylcarboxyl;

m is 0-5;

n is 0-5;

$R^4$ and $R^5$ are each independently selected from H, $C_1$-$C_6$, branched or unbranched alkyl, alkenyl, or alkynyl, $C_3$-$C_6$ saturated or unsaturated cyclic hydrocarbon, aryl, heteroaryl, haloalkyl, hydroxyl, alkoxyl, hydroxyalkyl, alkylcarbonyl, formyl, oxycarbonyl, carboxyl, alkyl carboxylate, alkylamide, alkylamino aminocarbonyl, or amino;

A is $CR^6_3$, $CXR^6_2$, $CX_2R^6$, $CX_3$, $COQ^1$, $SOQ^1$, $SO_2Q^1$, $CSQ^1$, amide, sulfonyl, sulfone, sulfonamide, sulfoxide, ester, thiocarbonyl, phenyl, substituted phenyl, heterocylic, heteroaromatic, cycloalkyl, and cycloalkenyl;

X is a halogen;

$R^6$ is H, $C_1$-$C_6$ straight or branched chain alkyl, alkenyl, or alkynyl, haloalkyl, perfluorinated alkyl, partially fluorinated alkyl, perhalogenated alkyl, partially halogenated alkyl;

$Q^1$ is an aryl or heteroaryl variably substituted with $(R^3)_n$, a phenyl, heteroaromatic or cycloalkyl, cycloalkenyl, or partially saturated or saturated heterocyclic ring a bicyclic compound, $NR^4R^5$;

$R^7$ is H, $C_1$-$C_6$ branched or unbranched alkyl, alkenyl, or alkynyl, haloalkyl, aryl, herteoaryl, perfluorinated alkyl and partially fluorinated alkyl, perhalogenated alkyl, partially perhalogenated alkyl, phenyl, cyano, ketyl, $CF_3$, substituted aryl or heteroaryl and spirocyclic compounds; and B is phenyl, aryl, heteroaromatic or cycloalkyl, cycloalkenyl, or partially saturated or saturated heterocyclic ring, or a bicyclic compound, with the proviso that when A is $CX_3$, B is not phenyl.

2. The compound according to claim 1 wherein
R$^1$ and R$^2$ are H;
C is aryl or heteroaryl having the structure wherein p is 0-1, and Z$^1$-Z$^6$ are each independently selected from C, N, O and S;
R$^3$ and R$^8$ are H, halogen;
m is 0-2;
n is 0-2;
A is COQ$^1$, SOQ$^1$, SO$_2$Q$^1$, CSQ$^1$, amide, sulfonyl, sulfone, sulfonamide, sulfoxide, ester, or thiocarbonyl;
Q$^1$ is an aryl or heteroaryl variably substituted with (R$^3$)$_n$, a phenyl, heteroaromatic or cycloalkyl, cycloalkenyl, or partially saturated or saturated heterocyclic ring a bicyclic compound, NR$^4$R$^5$; R$^7$ is H; and
B is phenyl, heteroaromatic or cycloalkyl, cycloalkenyl, or partially saturated or saturated heterocyclic ring, or a bicyclic compound.

3. The compound according to claim 2 wherein
wherein C is pyridyl;
A is COQ$^1$;
Q$^1$ is an aryl or heteroaryl variably substituted with (R$^3$)$_n$; and
B is phenyl or heteroaromatic.

4. The compound of claim 2 having a structure

5. The compound of claim 2 having a structure

6. The compound of claim 2 having a structure

7. The compound of claim 2 having a structure

8. The compound of claim 2 having a structure

9. The compound according to claim 1,
wherein R$^1$ and R$^2$ are H;
C is aryl or heteroaryl having the structure wherein p is 0 or 1, and Z$^1$-Z$^6$ are each independently selected from C, N, O and S;

$R^3$ and $R^8$ are halogen or methyl;

m is 0-2;

n is 0-2;

A is $CR^6_3$, $CXR^6_2$, $CX_2R^6$, $CX_3$;

X is a halogen;

$R^6$ is H, $C_1$-$C_6$ straight or branched chain alkyl, alkenyl, or alkynyl, haloalkyl, perfluorinated alkyl, partially fluorinated alkyl, perhalogenated alkyl, partially halogenated alkyl, phenyl, substituted phenyl, heteroaryl, cyano, or ketyl;

$R^7$ is H; and

B is phenyl, aryl, heteroaromatic or cycloalkyl, cycloalkenyl, or partially saturated or saturated heterocyclic ring, or a bicyclic compound, with the proviso that when A is $CX_3$, B is not phenyl.

10. The compound according to claim 9, wherein m is 1 or 2;

n is 1 or 2;

A is $CR^6_3$, $CXR^6_2$, $CX_2R^6$;

X is a halogen;

$R^6$ is perfluorinated alkyl or partially fluorinated alkyl; and

B is phenyl, aryl, or heteroaromatic.

11. The compound according to claim 10, wherein $R^3$ is bromine and $R^8$ is halogen or methyl.

12. The compound according to claim 11 having a structure

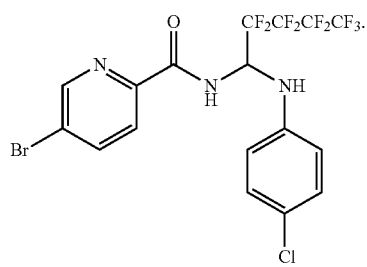

13. The compound according to claim 11 having a structure

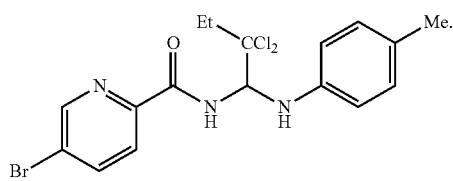

14. The compound according to claim 11 having a structure selected from

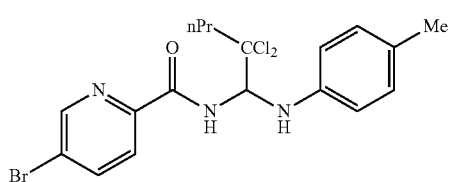

or

15. The compound according to claim 11 having a structure

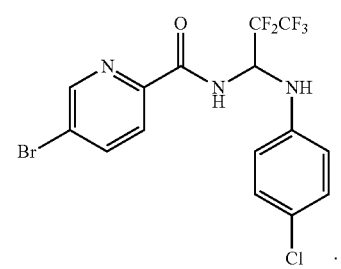

16. The compound according to claim 1 wherein $R^1$ and $R^2$ are H;

C is aryl or heteroaryl having the structure

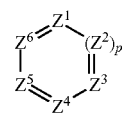

p is 0-1, and $Z^1$-$Z^6$ are each independently selected from C, N, O or S;

$R^3$ and $R^8$ are each independently selected from H, halogen;

m is 0-2;

n is 0-2;

A is phenyl, substituted phenyl, heterocylic, heteroaromatic, cycloalkyl, or cycloalkenyl;

$R^7$ is H; and

B is phenyl, aryl, heteroaromatic or cycloalkyl, cycloalkenyl, or partially saturated or saturated heterocyclic ring, or a bicyclic compound.

17. The compound of claim 16 having a structure selected from

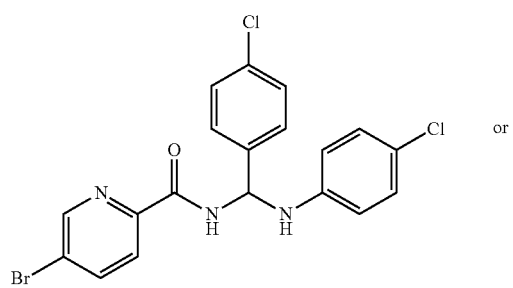

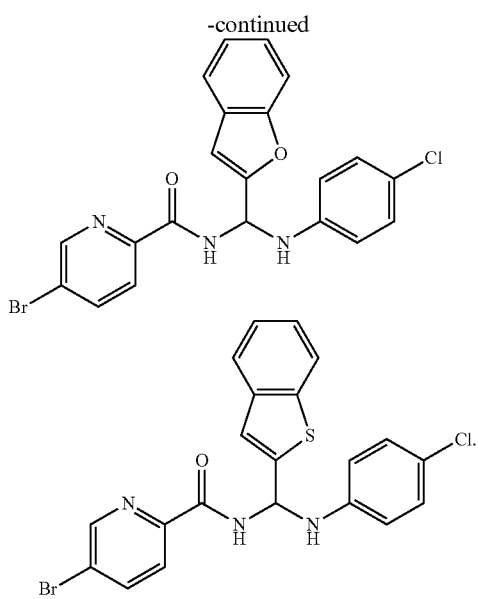
18. The compound according to claim 1 having a structure selected from
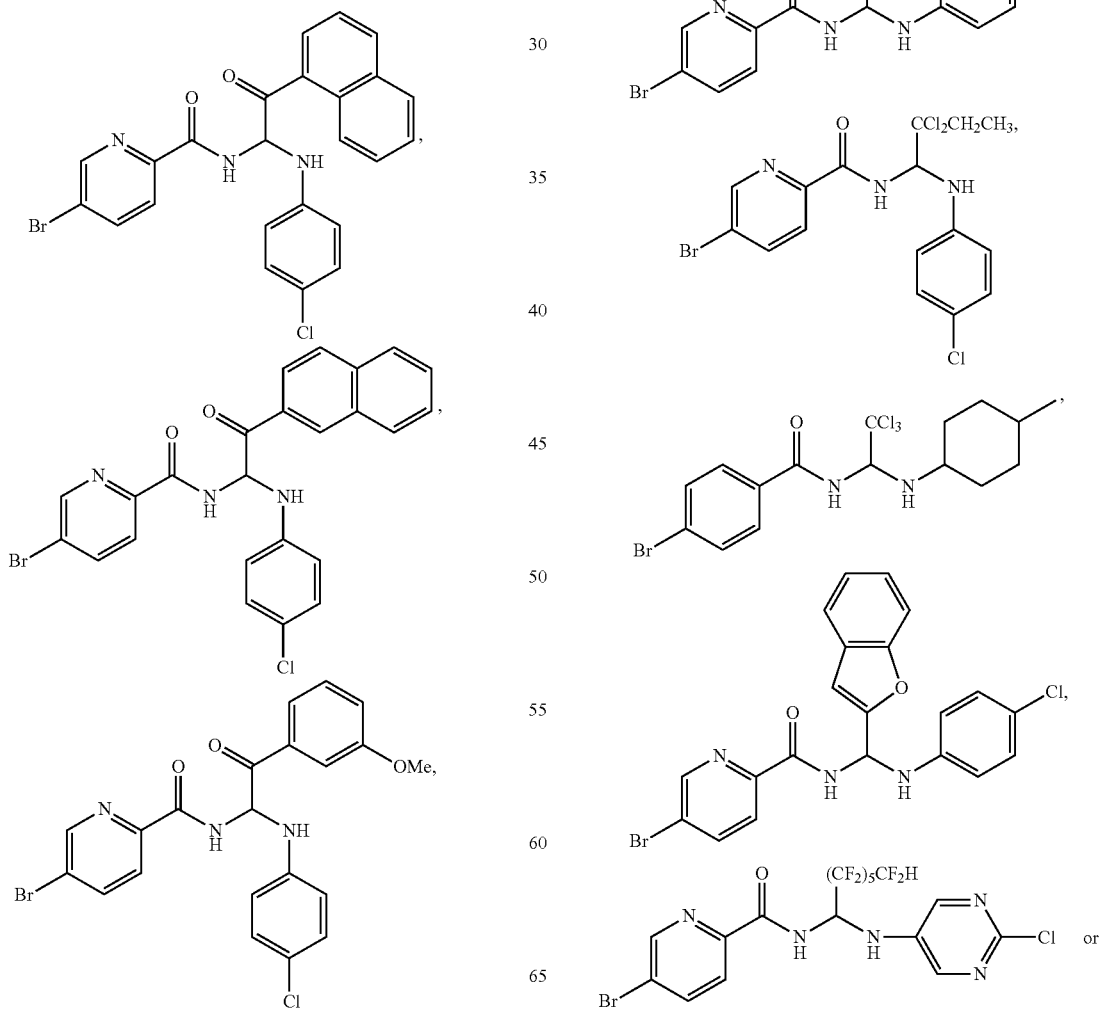

-continued
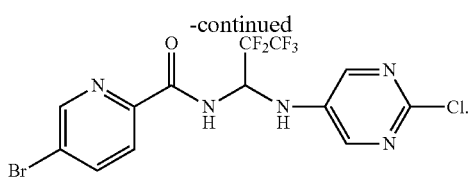
19. An ophthalmic composition comprising a pharmaceutically acceptable amount of a compound according to claim 1 and an excipient.
* * * * *

UNITED STATES PATENT AND TRADEMARK OFFICE
CERTIFICATE OF CORRECTION

| | | |
|---|---|---|
| PATENT NO. | : 8,168,795 B2 | Page 1 of 1 |
| APPLICATION NO. | : 12/852768 | |
| DATED | : May 1, 2012 | |
| INVENTOR(S) | : Phong X. Nguyen et al. | |

It is certified that error appears in the above-identified patent and that said Letters Patent is hereby corrected as shown below:

Please correct in claim 1 the following structure:

Delete " 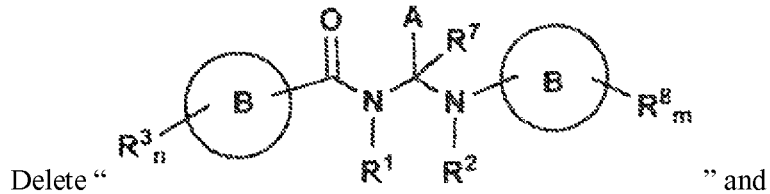 " and

Insert this structure -- 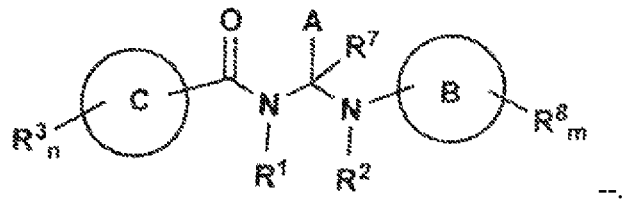 --.

Signed and Sealed this
Eleventh Day of September, 2012

David J. Kappos
Director of the United States Patent and Trademark Office